(12) United States Patent
Nilsen et al.

(10) Patent No.: US 7,323,325 B2
(45) Date of Patent: Jan. 29, 2008

(54) SHRIMP ALKALINE PHOSPHATASE

(75) Inventors: Inge Nilsen, Kvaloysletta (NO); Kersti Överbö, Kvaloysetta (NO); Olav Lanes, Tromsø (NO)

(73) Assignee: Biotec Pharmacon ASA, Tromso (NO)

( * ) Notice: Subject to any disclaimer, the term of this patent is extended or adjusted under 35 U.S.C. 154(b) by 483 days.

(21) Appl. No.: 10/399,026

(22) PCT Filed: Oct. 10, 2001

(86) PCT No.: PCT/GB01/04509

§ 371 (c)(1),
(2), (4) Date: Aug. 15, 2003

(87) PCT Pub. No.: WO02/31157

PCT Pub. Date: Apr. 18, 2002

(65) Prior Publication Data

US 2006/0234217 A1     Oct. 19, 2006

(30) Foreign Application Priority Data

Oct. 10, 2000 (GB) .................................. 0024827.8

(51) Int. Cl.
C12N 9/16     (2006.01)
C12N 1/19     (2006.01)
C12N 1/21     (2006.01)
C12N 5/06     (2006.01)
C12N 15/63    (2006.01)
C07H 21/04    (2006.01)

(52) U.S. Cl. .............. 435/196; 435/252.3; 435/254.11; 435/320.1; 435/325; 536/23.2

(58) Field of Classification Search .................... None
See application file for complete search history.

(56) References Cited

U.S. PATENT DOCUMENTS 5,741,676 A   4/1998   Fuller .......................... 435/911
5,756,285 A   5/1998   Fuller ........................... 435/6

FOREIGN PATENT DOCUMENTS

WO     WO 00/34476     6/2000

OTHER PUBLICATIONS

Nilsen et al. (Jul. 2001) Comparative Biochemistry and Physiology Part B, vol. 129, pp. 853-861.*
Kobori, H., et al., "Heat-labile Alkaline Phosphatase from Antarctic Bacteria: Rapid 5' End-Labeling of Nucleic Acids," *Proc. Natl. Acad. Sci.* USA 81:6691-6695, Nov. 1984.
Rina, M., et al., "Alkaline Phosphatase from the Antarctic Strain TAB5. Properties and Psychronphilic Adaptations," *Eur J Biochem.* 267(4):1230-8, Feb. 2000.

Ásgeirsson et al., "Alkaline phosphatase from Atlantic Cod (*Gadus morhua*). Kinetic and structural properties which indicate adaptation to low temperatures." *Comp. Biochem. Physiol.* 110B(2):315-329 (1995).
De Prada et al., "Purification and Characterization of Two Extracellular Alkaline Phosphatases from a Psycrophilic *Arthrobacter* Isolate." *Appl. Env. Microbiol* 63(7):2928-2931 (Jul. 1997).
Lee and Chuang, "Characterization of different molecular forms of alkaline phosphatase in the hepatopancreas from shrimp *Penaeus monodon* (Crustacea: Decapoda)." *Comp. Biochem. Physiol.* 99B(4):845-850 (1991).

(Continued)

*Primary Examiner*—Elizabeth Slobodyansky
(74) *Attorney, Agent, or Firm*—Seed IP Law Group PLLC

(57) ABSTRACT

The present invention relates to a nucleic acid molecule comprising a nucleotide sequence as set forth in SEQ ID Nos. 1 or 20 or having at least 55% sequence identify therewith and/or capable of hybridising under medium stringency conditions to the complementary sequence of SEQ ID Nos. 1 or 20, or the complementary sequence of said sequences, wherein said nucleotide sequence encodes or is complementary to a sequence which encodes a heat labile alkaline phosphatase and to a recombinant heat labile alkaline comprising: (a) all or a significant part of an amino acid sequence as shown in SEQ ID No. 2; or (b) all or a significant part of an amino acid sequence which has at least 60% sequence identify with SEQ ID No. 2 as well as methods for the manufacture thereof.

```
1
kAYWNKDAQDALDKQLGIKLREKQAKNVIFFLGDGMSLSTVTAARIYKGG
 5ReRP6:17

51
LTGKFEREKISWEEFDFAALSKTYNTDKQVTDSAASATAYLTGVKTNQGV
                              Active site

101
IGLDANTVRTNCSYQLDESLFTYSIAHWFQEAGRSTGVVTSTRVTHATPA

151
GTYAHVADRDWENDSDVVHDREDPEICDDIAEQLVFREPGKNFKVIMGGG
                                          5ReRP6:26

201
RRGFFPEEALDIEDGIPGEREDGKHLITDWLDDKASQGATASYVWNRDDL
                       H23:30

251
LAVDIRNTDYLMGLFSYTHLDTVLTRDAEMDPTLPEMTKVAIEMLTKDEN

301
GFFLLVEGGRIDHMHHANQIRQSLAETLDMEEAVSMALSMTDPEETIILV

351
TADHGHTLTITGYADRNTDILDFAGISDLDDRRYTILDYGSGPGYHITED

401
GKRYEPTEEDLKDINFRYASAAPKHSVTHDGTDVGIWVNGPFAHLFTGVY
                  H23:18

451
EENYIPHALAYAACVGTGRTFCDEK *
```

17 Claims, 11 Drawing Sheets

OTHER PUBLICATIONS

Olsen et al., "Alkaline phosphatase from the hepatopancreas of shrimp (*pandalus borealis*): a dimeric enzyme with catalytically active subunits." *Biochem. Physiol.* 99B(4):755-761 (1991).

Olsen et al., "Recovery of Enzymes from Shrimp Waste." *Process Biochem.* 25:67-68 (Apr. 1990).

Shandilya and Chatterjee, "An engineered thermosensitive alkaline phosphate for dephosphorylating DNA." *Focus* 17(3):93-95 (1995).

Whitmore and Goldberg. "Trout intestinal alkaline phosphatases. II. The effect of temperature upon enzymatic activity in vitro and in vivo." *J. Exp. Zool.* 182(1):59-68 (1972).

\* cited by examiner

Fig.1. [SEQ I.D. NO. 1]

```
GATGCCCAAGATGCACTGGATAAACAGCTGGGATAAAACTGCGAGAGAAGCAGGCCAAGAACGTGATCTTCTTCCTAGG   - 80
AGACGGGATGTCCCTCAGTACGCAGTTACCGCAGCAAGAATCTACAAAGGTGGATTGACCGGGAAATTTGAACGGGAAAGA  - 160
TTTCGTGGGAAGAATTCGACTTTGCTGCTTTGAGTAAGACGTACAATACGGACAAGCAAGATGACAGATAGTCTGCCAGT  - 240
GCCACAGCCTACCTCACTGGGGTGAAGACCAACCAGGAGTCATCGGCCTTGATGCCAATACCGTGAGAACAAACTGCTC   - 320
TTACCAACTTGATGAATCCCTCTCACTTACTCCATCGCCCATTGGTTCCAGGAGGCTGGCAGATCAACAGGTGTCGTGA   - 400
CATCGACCAGGTAACTCATCGTACTCCTGCAGGAACTTATGCTCACGTGGCTGACAGAGATTGGGAGAACGACAGTGAT   - 480
GTTGTCCACGACAGAGAAGATCCAGAAGAATATGTGATGACATAGCTGAACAACTGGTATTCAGAGAACCTGAAAGAACTT  - 560
CAAGGTCATCATGGGCGGCGCTGGGCGTGGATTCTTCCTGAGGAAGCGCTTGATATCGAAGATGCATTCCAGGGGAAA    - 640
GGGAAGATGCCAAACACCTCATAACCGATTGGTTGGACGCATCTCAGGAGCCACAGCATCGTATGTCTGGAAC       - 720
CGAGATGATCTATTGGCTGTTGACATTCGAAACACAGACTACCTTATGGACTGTTTCATACACACATCTAGACACAGT   - 800
TTTAACCAGAGACGCCGAAATGGATCCCACCTTGCCGGAAATGACAAAGGTGCCATCGAAATGCTGACGAAGGATGAAA   - 880
ATGGCTTTTCCTCTTAGTAGAAGGTGGACGGATTGACCATATGCACCGCCAATCAGATCCGTCAGTCGTTAGCGGAG   - 960
ACGCTGGACATGGAGAAAGTCTATCCATGGCTCTCTCTATGACAGACAGAGAACCAGAGAAACAATCATTTCTGGGTCACAGC - 1040
TGATCACGGTCACACTCTCACCATCACTGGATACGCAGACAGAAGCAGGGACCTGGATATTTTGGATTTCGCCGGCATCAGGGACT - 1120
TGGATGATAGGAGGTACACCATCCTGGACTATGGCAGTGACCTGGATATCATATCACGGAAGATGGCAAACGTTACGAA    - 1200
CCTACAGAGGAAGATTTGAAAGACATCAATTCCGCTACGCATCGGCAGCCCAAGCATTCAGTTACCATGATGGCAC     - 1280
AGAGGTTGGTATTTGGGTCAACGACCTTTCGCTCATCTCTTCACGGTCACGGGTGTCTATGAAGAGAATTACATTCCCC   - 1360
ACGCCTTGGCCTACGCAGCCTGCGTTGGTACAGGACGCCACTTTCTGTGACGAAAAATGAGATGTAGATGATTACCTTCTT - 1440
AAGTACATTAAAGATTGCAAAAAAAAAAAAAAAAAAAAAAA    - 1481
```

Fig.2. [SEQ I.D. NO. 2]

```
  1  KAYWNKDAQDALDKQLGIKLREKQAKNVIFFLGDGMSLSTVTAARIYKGG
     ─────────
     5ReRP6:17
 51  LTGKFEREKISWEEFFAALSKTYNTDKQVFDSAASATAYLTGVKTNQGV
                                    ───────────
                                    Active site
101  IGLDANTVRTNCSYQLDESLFTYSIAHWFQEAGRSTGVVTSTRVTHATPA
151  GTYAHVADRDWENDSDVVHDREDPEICDDIAEQLVFREPGKNFKVIMGGG
                                              ─────────
                                              5ReRP6:26
201  RRGFFP EEALDIEDGIPGEREDGKHLITDWLDDKASQGATASYVWNRDDL
     ──────                    ────────────────
                                   H23:30
251  LAVDIRNTDYLMGLFSYTHLDTVLTRDAEMDPTLPEMTKVAIEMLTKDEN
301  GFFLLVEGGRIDHMHHANQIRQSLAETLDMEESCIHGSLYDRPRGNNHFW
351  VTADHGHTLTITGYADRNTDILDFAGISDLDDRRYTILDYGSPGYHITE
401  DGKRYEPTEEDLKDINERYASAAPKHSVTHDGTDVGIWVNGPFAHLFTVT
                  ──────────────
                      H23:18
451  GVYEENYIPHALAYAACVGTGRTFCDEK stop      - 478
```

Fig.3.

```
                         *         20         *         40         *         60         *
ppbt_mouse  : ----------------MISPFLVLAIGTCLTNSFVPEKERDPSY RQQ  ETLKNALRLQKLN---TNV   V  :  54
ppbt_human  : ----------------MISPFLVLAIGTCLTNSLVPEKEKDPKY RDQ  ETLKYALELQKLN---TNV   V  :  54
alpchicken  : ----------------MKAFLLTLLAQLCSASLVPEREKDPEY RQQ  ETLRDALRLQHLN---QNV   L  :  53
sap         : -------------------------------KAY  NKD  DALDKQLGIKLP----EKQ   V     :  28
ppb_bommo   : HVVSVVAAAAAAGLVRAEDRYHPERLAAGEASAATRSAAESEASF VRE  E AIERREREGAGAKQAAGH KW  :  74
                                                        U   AQ                      AKN

*         80         *        100         *        120         *        140
ppbt_mouse  : I   LGDGDGVS  VT AP ILK GQLHHNTG ETRLEHDK PFV SK T NTNA QV PDS AGTATAYL CGV  N  GTV :  128
ppbt_human  : I   LGDGDGVS  VT AP ILK GQLHHNP G ETRLEHDK PFV SK T NTKA QV PDS AGTATAYL CGV  N  GTV :  128
alpchicken  : IL  LGDGHGVS  VT AP ILK GQLQHRKG ESLLEKD K  PTV  K T  TNA QV PDE AGTATAYL CGV  N  GTV :  127
sap         : IF  LGDGHSLS  VT AB IYK GGLTG-KF REKISWEE DF AA SK T NTDE QV TDS  AS ATAYL TGV  D  GVI :  101
ppb_bommo   : VM  LGDG SVP  LA  A TLL GQRRGQTG EA SLHFEQ PTLG A T CVNA QV PDS  CT ATAYL CGV  N  QGTP :  148
              FLGDGR   T   AAR    G         E      F     L   KTY     QV  DS    ATAYL  GVK N  G

*        160         *        180         *        200         *        220
ppbt_mouse  : GVS ATE TR  NTTQGN--EVT  LR AKD  CKSVG IV  T VN  AT PS AAY HS AD D  YS NEHPPEALS-Q :  199
ppbt_human  : GVS AATE SR NTTQGN--EVT  LR AKD  CKSVG IV  T VN  AT PS AAY HS AD D  YS NEHPPEALS-Q :  199
alpchicken  : GVS  GVT DR NTTKGQ--EVT  LR AKDE  KAV G IV  T V  AT PS AAY HS AN RD  YS GEHPLDALE-G :  198
sap         : GLD NTV IN  SYQLDESLFTYS AH  FQE  CRSTG VV  S V  A  TP AGTY HV  D  DDEN DSDVVHDREDPE :  175
ppb_bommo   : GVT  AVP HD  EASTDVTKRVQS AE AL AD RDV G IV  T IT AS AGTF KV  N  EN DVKQEGHDVN :  222
              G A       R C              SI  W  G    G VT  TR  HA  P       A  AR W  D

*        240         *        260         *        280         *
ppbt_mouse  : G  RD IA  QL HHN--IKDID   GGGR KYHY RNRTD V  YELDEKARGT RLD GLD  ISI  KSF P-RHKHSHYV  :  270
ppbt_human  : G  RD IA  QL HHN--IRDID   GGGR KYHY RNKTD V  YESDEKARGT RLD GLD  VDT  KSF P-RHKHSHF I  :  270
alpchicken  : G  RD IA  Q  VDN--IPDIE  L GGGR KYHF PKNTS V  YPQEERERGT RL  KD   VQA  HDT P-AGKV KYV  :  269
sap         : I  DD IA  Q   VFREPGKNFK   E GGG  RGFF   EEALD  D GIP----GE ED  K     ITD LDD  SQGATASTV  :  245
ppb_bommo   : F   DI  Q  IKMAPGNKFK    IGGG REF L TTQV E GTRG-----LR DR N  IEE QND ESQKV YKYL    :  291
              C   DIA  QL            VI  GGGR       P     D  E         R  DG   L     W  K              V

*        300         *        320         *        340         *        360
ppbt_mouse  : M TE LL ALDPSRV Y L GL  EPGDHQYE NRNWLTD PS  S HVE AL RI TKNL  GFFL L EGGRIDH GH EGK :  344
ppbt_human  : M TE LL TLDPHNV DY L GL  EPGDHQYE NRNWVTD PS S B VVA IQI RKNP  GFFL L EGGRIDH GH EGK :  344
alpchicken  : H RE LL ALNVSRV F L GL  EPGDHVYE DPNNETD PS S  HVA A IRW OKNP  GFFL L EGGRIDH GH EGK :  343
sap         : N DD LA  AVDIRNTD YL GL  SYTHLDTV   PRD AEHD TQ PRH TKA IEH  TKD ENGFFL  EGGRIDH EH  ANQ :  319
ppb_bommo   : M  QE LL KLGSSPPDY L GL  EGSHLQYE EGDESTE  TL A LTDV IRW  SRNER GFFL F EGGRIDE  H HH DNY :  365
              R   LL            D L  GLF           L            PLE   VA     L     GFFL  VEGGRIDH  HH

*        380         *        400         *        420         *        440
ppbc_mouse  : AKQA H  AVEHDQAIGRAG AKTSQK-DTLTVV TADES EVFTFG Y TP GHSIFGLAPHVS DTDKKPFTAIL GN :  417
ppbt_human  : AKQA H  AVEHDRAIGQAGSLTSSE-DTLTV V TADES EVFTFG Y TP GNSIFGLAPHLS DTDKKPFTAIL GN :  417
alpchicken  : AKQA H  AVELDRAVGLAGRPLTSPR-DTLSV V TADHS EVFTFG Y TP GNPIFGLAPHSO DVDRKPFTSIL GN :  416
sap         : IRQS  A  TLDHEESCIEHGSLYDRPRGMNH FW TADH G HTLTIT GY AD RNTDILDFAGIS- DL DDRRYTILD GS :  392
ppb_bommo   : AHLA  D  TIEHDRAVKVATD ALKED-ESLVV V TADH  VHSF L GY SP RGTDVLGTVRSL- DS NRHPF WVLS TN :  437
              L  E                            VTADH  H         GY   R                  D          Y

*        460         *        480         *        500         *     S
ppbt_mouse  : GPG YKVVD- GE  -ENVSHVDYAHNNYQAQSAVPLRHE TH GGED VAVF A  PHAHLLHG--VP QNY I  VH  YA :  487
ppbt_human  : GPG YKVVG- GE  -ENVSHVDYAHNNYQAQSAV LRHE TH GGED VAVFS  PNAHLLHG--VP QNY VP VH YA :  487
alpchicken  : GPG YKIVG- GE  -ENVSAVDF AHANY QAQAAV LRQE  TH GGED VAVF AR PNAHLLHG--VM QNY IP HA YA :  486
sap         : GPG YHITED GK  -YEPTEEDLKD INFRY AS AA KHSV  TD  D GIUVH GPF AHLFTVTGV  ENY IPHAL YA :  465
ppb_bommo   : GPG ARIQQN  VR PDVTTDANFGALRWRTHTDV LDSE  TH  GGED V TVF AL  VHHW HFSG--LY QTH VP HR  L :  509
              GPG              G R                    P  TH G  DV    G          E        PH  A  A 20         *        540         *
ppbt_mouse  : S  IG ANLDH  AV GSGSAPSPGALLLLPLAVLSLPTLF- :  524
ppbt_human  : A  IG ANLGH  AP ASSAGSLAAGPLLLALALYPLSVLF- :  524
alpchicken  : A  IG PNRAH  SS AARPAATATLLPVLLLLLLLC----- :  519
sap         : AC  GTGRTF  DEK------------------------- :  478
ppb_bommo   : A   GPGRHV  V SAATVPTAALLSLLLAAFITLRHQCFL :  547
              C    G         C
```

Fig.4.

```
AArGCnTAyTGGAAyAArGATGCCCAAGATGCACTGGATAAACAGCTGGGGATAAAACTG    60
CGAGAGAAGCAGGCCAAGAACGTGATCTTCTTCCTAGGAGACGGGATGTCCCTCAGTACA   120
GTTACCGCAGCAAGAATCTACAAAGGTGGATTGACCGGGAAATTTGAACGGGAAAAGATT   180
TCGTGGGAAGAATTCGACTTTGCTGCTTTGAGTAAGACGTACAATACGGACAAGCAAGTG   240
ACAGATAGTGCTGCCAGTGCCACAGCCTACCTCACTGGGGTGAAGACCAACCAGGGAGTC   300
ATCGGCCTTGATGCCAATACCGTGAGAACAAACTGCTCTTACCAACTTGATGAATCCCTC   360
TTCACTTACTCCATCGCCCATTGGTTCCAGGAGGCTGGCAGATCAACAGGTGTCGTGACA   420
TCGACCAGGGTAACTCATGCTACTCCTGCAGGAACTTATGCTCACGTGGCTGACAGAGAT   480
TGGGAGAACGACAGTGATGTTGTCCACGACAGAGAAGATCCAGAAATATGTGATGACATA   540
GCTGAACAACTGGTATTCAGAGAACCTGGAAAGAACTTCAAGGTCATCATGGGCGGCGGT   600
CGGCGTGGATTCTTTCCTGAGGAAGCGCTTGATATCGAAGATGGCATTCCAGGGGAAAGG   660
GAAGATGGCAAACACCTCATAACCGATTGGTTGGACGATAAGGCATCTCAGGGAGCCACA   720
GCATCGTATGTCTGGAACCGAGATGATCTATTGGCTGTTGACATTCGAAACACAGACTAC   780
CTTATGGGACTGTTTTCATACACACATCTAGACACAGTTTTAACCAGAGACGCCGAAATG   840
GATCCCACCTTGCCGGAAATGACAAAGGTCGCCATCGAAATGCTGACGAAGGATGAAAAT   900
GGCTTTTTCCTCTTAGTAGAAGGTGGACGGATTGACCATATGCACCACGCCAATCAGATC   960
CGTCAGTCGTTAGCGGAGACGCTGGACATGGAGGAAGCTGTATCCATGGCTCTCTCTATG  1020
ACAGACCCAGAGGAAACAATCATTCTGGTCACAGCTGATCACGGTCACACTCTCACCATC  1080
ACTGGATACGCAGACAGGAACACCGATATTTTGGATTTCGCCGGCATCAGCGACTTGGAT  1140
GATAGGAGGTACACCATCCTGGACTATGGCAGTGGACCTGGATATCATATCACGGAAGAT  1200
GGCAAACGTTACGAACCTACAGAGGAAGATTTGAAAGACATCAATTTCCGCTACGCATCG  1260
GCAGCGCCCAAGCATTCAGTTACCCATGATGGCACAGACGTTGGTATTTGGGTCAACGGA  1320
CCTTTCGCTCATCTCTTCACGGGTGTCTATGAAGAGAATTACATTCCCCACGCCTTGGCC  1380
TACGCAGCCTGCGTTGGTACAGGACGCACTTTCTGTGACGAAAAATGAGATGTAGATGAT  1440
TACCTTCTTAAGTACATTAAAGATTGC-(A)23                             1490
```

Fig.5.

```
  1 kAYWNKDAQDALDKQLGIKLREKQAKNVIFFLGDGMSLSTVTAARIYKGG
    5ReRP6:17
 51 LTGKFEREKISWEEFDFAALSKTYNTDKQVTDSAASATAYLTGVKTNQGV
                                 Active site
101 IGLDANTVRTNCSYQLDESLFTYSIAHWFQEAGRSTGVVTSTRVTHATPA 151 GTYAHVADRDWENDSDVVHDREDPEICDDIAEQLVFREPGKNFKVIMGGG
                                                5ReRP6:26
201 RRGFFPEEALDIEDGIPGEREDGKHLITDWLDDKASQGATASYVWNRDDL
                            H23:30
251 LAVDIRNTDYLMGLFSYTHLDTVLTRDAEMDPTLPEMTKVAIEMLTKDEN

301 GFFLLVEGGRIDHMHHANQIRQSLAETLDMEEAVSMALSMTDPEETIILV

351 TADHGHTLTITGYADRNTDILDFAGISDLDDRRYTILDYGSGPGYHITED

401 GKRYEPTEEDLKDINFRYASAAPKHSVTHDGTDVGIWVNGPFAHLFTGVY
                H23:18
451 EENYIPHALAYAACVGTGRTFCDEK  *
```

```
1    AArGCnTAyTGGAAyAArGATGCCCAAGATGCACTGGATAAACAG  45
     |||||||||||||||||||||||||||||||||||||||||||||
1    AArGCnTAyTGGAAyAArGATGCCCAAGATGCACTGGATAAACAG  45

46   CTGGGGATAAAACTGCGAGAGAAGCAGGCCAAGAACGTGATCTTC  90
     |||||||||||||||||||||||||||||||||||||||||||||
46   CTGGGGATAAAACTGCGAGAGAAGCAGGCCAAGAACGTGATCTTC  90

91   TTCCTAGGAGACGGGATGTCCCTCAGTACAGTTACCGCAGCAAGA  135
     |||||||||||||||||||||||||||||||||||||||||||||
91   TTCCTAGGAGACGGGATGTCCCTCAGTACAGTTACCGCAGCAAGA  135

136  ATCTACAAAGGTGGATTGACCGGGAAATTTGAACGGGAAAAGATT  180
     |||||||||||||||||||||||||||||||||||||||||||||
136  ATCTACAAAGGTGGATTGACCGGGAAATTTGAACGGGAAAAGATT  180

181  TCGTGGGAAGAATTCGACTTTGCTGCTTTGAGTAAGACGTACAAT  225
     |||||||||||||||||||||||||||||||||||||||||||||
181  TCGTGGGAAGAATTCGACTTTGCTGCTTTGAGTAAGACGTACAAT  225

226  ACGGACAAGCAAGTGACAGATAGTGCTGCCAGTGCCACAGCCTAC  270
     |||||||||||||||||||||||||||||||||||||||||||||
226  ACGGACAAGCAAGTGACAGATAGTGCTGCCAGTGCCACAGCCTAC  270

271  CTCACTGGGGTGAAGACCAACCAGGGAGTCATCGGCCTTGATGCC  315
     |||||||||||||||||||||||||||||||||||||||||||||
271  CTCACTGGGGTGAAGACCAACCAGGGAGTCATCGGCCTTGATGCC  315

316  AATACCGTGAGAACAAACTGCTCTTACCAACTTGATGAATCCCTC  360
     |||||||||||||||||||||||||||||||||||||||||||||
316  AATACCGTGAGAACAAACTGCTCTTACCAACTTGATGAATCCCTC  360

361  TTCACTTACTCCATCGCCCATTGGTTCCAGGAGGCTGGCAGATCA  405
     |||||||||||||||||||||||||||||||||||||||||||||
361  TTCACTTACTCCATCGCCCATTGGTTCCAGGAGGCTGGCAGATCA  405

406  ACAGGTGTCGTGACATCGACCAGGGTAACTCATGCTACTCCTGCA  450
     |||||||||||||||||||||||||||||||||||||||||||||
406  ACAGGTGTCGTGACATCGACCAGGGTAACTCATGCTACTCCTGCA  450

451  GGAACTTATGCTCACGTGGCTGACAGAGATTGGGAGAACGACAGT  495
     |||||||||||||||||||||||||||||||||||||||||||||
451  GGAACTTATGCTCACGTGGCTGACAGAGATTGGGAGAACGACAGT  495

496  GATGTTGTCCACGACAGAGAAGATCCAGAAATATGTGATGACATA  540
     |||||||||||||||||||||||||||||||||||||||||||||
496  GATGTTGTCCACGACAGAGAAGATCCAGAAATATGTGATGACATA  540

541  GCTGAACAACTGGTATTCAGAGAACCTGGAAAGAACTTCAAGGTC  585
     |||||||||||||||||||||||||||||||||||||||||||||
541  GCTGAACAACTGGTATTCAGAGAACCTGGAAAGAACTTCAAGGTC  585

586  ATCATGGGCGGCGGTCGGCGTGGATTCTTTCCTGAGGAAGCGCTT  630
     |||||||||||||||||||||||||||||||||||||||||||||
586  ATCATGGGCGGCGGTCGGCGTGGATTCTTTCCTGAGGAAGCGCTT  630

631  GATATCGAAGATGGCATTCCAGGGGAAAGGGAAGATGGCAAACAC  675
     |||||||||||||||||||||||||||||||||||||||||||||
631  GATATCGAAGATGGCATTCCAGGGGAAAGGGAAGATGGCAAACAC  675
```

Fig.7 (Cont i).

```
676   CTCATAACCGATTGGTTGGACGATAAGGCATCTCAGGGAGCCACA 720
      |||||||||||||||||||||||||||||||||||||||||||||
676   CTCATAACCGATTGGTTGGACGATAAGGCATCTCAGGGAGCCACA 720

721   GCATCGTATGTCTGGAACCGAGATGATCTATTGGCTGTTGACATT 765
      |||||||||||||||||||||||||||||||||||||||||||||
721   GCATCGTATGTCTGGAACCGAGATGATCTATTGGCTGTTGACATT 765

766   CGAAACACAGACTACCTTATGGGACTGTTTTCATACACACATCTA 810
      |||||||||||||||||||||||||||||||||||||||||||||
766   CGAAACACAGACTACCTTATGGGACTGTTTTCATACACACATCTA 810

811   GACACAGTTTTAACCAGAGACGCCGAAATGGATCCCACCTTGCCG 855
      |||||||||||||||||||||||||||||||||||||||||||||
811   GACACAGTTTTAACCAGAGACGCCGAAATGGATCCCACCTTGCCG 855

856   GAAATGACAAAGGTCGCCATCGAAATGCTGACGAAGGATGAAAAT 900
      |||||||||||||||||||||||||||||||||||||||||||||
856   GAAATGACAAAGGTCGCCATCGAAATGCTGACGAAGGATGAAAAT 900

901   GGCTTTTTCCTCTTAGTAGAAGGTGGACGGATTGACCATATGCAC 945
      |||||||||||||||||||||||||||||||||||||||||||||
901   GGCTTTTTCCTCTTAGTAGAAGGTGGACGGATTGACCATATGCAC 945

946   CACGCCAATCAGATCCGTCAGTCGTTAGCGGAGACGCTGGACATG 990
      |||||||||||||||||||||||||||||||||||||||||||||
946   CACGCCAATCAGATCCGTCAGTCGTTAGCGGAGACGCTGGACATG 990

991   GAGG.AAGCTGTATCCATGGCTCTCTCTATGACAGACCCAGAGGA 1034
      ||||  |||||||||||||||||||||||||||||||||||||||
991   GAGGAAAGCTGTATCCATGGCTCTCTCTATGACAGACCCAGAGGA 1035

1035  AACAATCA.TTCT.GGTCACAGCTGATCACGGTCACACTCTCACC 1077
      ||||||||  ||| |||||||||||||||||||||||||||||||
1036  AACAATCATTTCTGGGTCACAGCTGATCACGGTCACACTCTCACC 1080

1078  ATCACTGGATACGCAGACAGGAACACCGATATTTTGGATTTCGCC 1122
      |||||||||||||||||||||||||||||||||||||||||||||
1081  ATCACTGGATACGCAGACAGGAACACCGATATTTTGGATTTCGCC 1125

1123  GGCATCAGCGACTTGGATGATAGGAGGTACACCATCCTGGACTAT 1167
      |||||||||||||||||||||||||||||||||||||||||||||
1126  GGCATCAGCGACTTGGATGATAGGAGGTACACCATCCTGGACTAT 1170

1168  GGCAGTGGACCTGGATATCATATCACGGAAGATGGCAAACGTTAC 1212
      |||||||||||||||||||||||||||||||||||||||||||||
1171  GGCAGTGGACCTGGATATCATATCACGGAAGATGGCAAACGTTAC 1215

1213  GAACCTACAGAGGAAGATTTGAAAGACATCAATTTCCGCTACGCA 1257
      |||||||||||||||||||||||||||||||||||||||||||||
1216  GAACCTACAGAGGAAGATTTGAAAGACATCAATTTCCGCTACGCA 1260

1258  TCGGCAGCGCCCAAGCATTCAGTTACCCATGATGGCACAGACGTT 1302
      |||||||||||||||||||||||||||||||||||||||||||||
1261  TCGGCAGCGCCCAAGCATTCAGTTACCCATGATGGCACAGACGTT 1305

1303  GGTATTTGGGTCAACGGACCTTTCGCTCATCTCT......TCACG 1341
      ||||||||||||||||||||||||||||||||||      |||||
1306  GGTATTTGGGTCAACGGACCTTTCGCTCATCTCTTCACGGTCACG 1350

1342  GGTGTCTATGAAGAGAATTACATTCCCCACGCCTTGGCCTACGCA 1386
      |||||||||||||||||||||||||||||||||||||||||||||
1351  GGTGTCTATGAAGAGAATTACATTCCCCACGCCTTGGCCTACGCA 1395

1387  GCCTGCGTTGGTACAGGACGCACTTTCTGTGACGAAAAATGAGAT 1431
      |||||||||||||||||||||||||||||||||||||||||||||
1396  GCCTGCGTTGGTACAGGACGCACTTTCTGTGACGAAAAATGAGAT 1440
```

Fig. 7 (Cont ii).

```
1432  GTAGATGATTACCTTCTTAAGTACATTAAAGATTGCAAAAAAAAA  1476
      |||||||||||||||||||||||||||||||||||||||||||||
1441  GTAGATGATTACCTTCTTAAGTACATTAAAGATTGCAAAAAAAAA  1485

1477  AAAAAAAAAAAAAA                                 1490
      ||||||||||||||
1486  AAAAAAAAAAAAAA                                 1499
```

Fig. 8.

```
1    KAYWNKDAQDALDKQLGIKLREKQAKNVIFFLGDGMSLSTVTAAR  45
     ||||||||||||||||||||||||||||||||||||||||||||
1    KAYWNKDAQDALDKQLGIKLREKQAKNVIFFLGDGMSLSTVTAAR  45

46   IYKGGLTGKFEREKISWEEFDFAALSKTYNTDKQVTDSAASATAY  90
     ||||||||||||||||||||||||||||||||||||||||||||
46   IYKGGLTGKFEREKISWEEFDFAALSKTYNTDKQVTDSAASATAY  90

91   LTGVKTNQGVIGLDANTVRTNCSYQLDESLFTYSIAHWFQEAGRS  135
     ||||||||||||||||||||||||||||||||||||||||||||
91   LTGVKTNQGVIGLDANTVRTNCSYQLDESLFTYSIAHWFQEAGRS  135

136  TGVVTSTRVTHATPAGTYAHVADRDWENDSDVVHDREDPEICDDI  180
     ||||||||||||||||||||||||||||||||||||||||||||
136  TGVVTSTRVTHATPAGTYAHVADRDWENDSDVVHDREDPEICDDI  180

181  AEQLVFREPGKNFKVIMGGGRRGFFPEEALDIEDGIPGEREDGKH  225
     ||||||||||||||||||||||||||||||||||||||||||||
181  AEQLVFREPGKNFKVIMGGGRRGFFPEEALDIEDGIPGEREDGKH  225

226  LITDWLDDKASQGATASYVWNRDDLLAVDIRNTDYLMGLFSYTHL  270
     ||||||||||||||||||||||||||||||||||||||||||||
226  LITDWLDDKASQGATASYVWNRDDLLAVDIRNTDYLMGLFSYTHL  270

271  DTVLTRDAEMDPTLPEMTKVAIEMLTKDENGFFLLVEGGRIDHMH  315
     ||||||||||||||||||||||||||||||||||||||||||||
271  DTVLTRDAEMDPTLPEMTKVAIEMLTKDENGFFLLVEGGRIDHMH  315

316  HANQIRQSLAETLDMEEAVSMALSMTDPE.ETIILVTADHGHTLT  359
     ||||||||||||||||:       |        |||||||||||
316  HANQIRQSLAETLDMEESCIHGSLYDRPRGNNHFWVTADHGHTLT  360

360  ITGYADRNTDILDFAGISDLDDRRYTILDYGSPGYHITEDGKRY  404
     |||||||||||||||||||||||||||||||||||||||||||
361  ITGYADRNTDILDFAGISDLDDRRYTILDYGSPGYHITEDGKRY  405

405  EPTEEDLKDINFRYASAAPKHSVTHDGTDVGIWVNGPFAHLF..T  447
     ||||||||||||||||||||||||||||||||||||||||||  |
406  EPTEEDLKDINFRYASAAPKHSVTHDGTDVGIWVNGPFAHLFTVT  450

448  GVYEENYIPHALAYAACVGTGRTFCDEK                 475
     ||||||||||||||||||||||||||||
451  GVYEENYIPHALAYAACVGTGRTFCDEK                 478
```

```
            1         11        21        31        41        51        61
    1   ATGAGGGCTTTCTACTGTCTATTTGGGTTACTTTTAACCCTAAGTCTTCAAGGAGAAGCAACACGTCAAC
 1(+1)   M  R  A  F  Y  C  L  F  G  L  L  L  T  L  S  L  Q  G  E  A  T  R  Q

71   CAAGTTCCTATGATGGAGATGAGTACCACGAGAGATATCCGGGTCAATCCAACCCCATAACAGAAGAAGA
24(+1)   P  S  S  Y  D  G  D  E  Y  H  E  R  Y  P  G  Q  S  N  P  I  T  E  E  D

141   C
48(+1)
```

SHRIMP ALKALINE PHOSPHATASE

CROSS-REFERENCE TO RELATED APPLICATIONS

This application claims the benefit under 35 U.S.C. § 371 of PCT/GB01/04509 filed Oct. 10, 2001; and under 35 U.S.C. § 119(a) of GB Patent Application No. 0024827.8 filed Oct. 10, 2000, where these applications are incorporated herein by reference in their entireties.

BACKGROUND OF THE INVENTION (1) Field of the Invention

The present invention relates to the enzyme alkaline phosphatase and more particularly to this enzyme derived from *Pandalus borealis* and to nucleic acid molecules encoding it.

(2) Description of Related Art

Alkaline phosphatases (E.C. 3.1.3.1), having the alternative names alkaline phosphomonoesterase, phosphomonoesterase or glycerophosphatase, are orthophosphoric-monoester phosphohydrolases with enzyme activity optima at alkaline conditions. Examples of alkaline phosphatase (ALP) substrates are DNA, RNA, and ribo-as well as deoxyribonucleoside triphosphates. The hydrolysis produces an alcohol and an orthophosphate. In other words, ALPs dephosphorylate DNA, RNA, rNTPs and dNTPs. Dephosphorylation of protein by various ALPs have also been reported. ALPs are widespread in nature, found in organisms ranging from bacteria to humans. Complex organisms usually contain both tissue-specific and non-specific ALPs. The polypeptides differ in size from 15 to 170 kDa. Some of these proteins are bound or "anchored" to cellular membranes. Most commonly the enzymes have a requirement for divalent metal cations such as $Mg^{2+}$ or $Zn^{2+}$.

Current usage of ALPs in molecular biology is focused on, but not limited to, three main applications of DNA analysis or preparation: 1) dephosphorylation of vector DNA after restriction enzyme digestions to minimise self-ligation of the cloning vector, thus favouring ligation of insert to the vector and creating a recombinant construct, 2) dephosphorylation of dNTPs after PCR amplifications, in combined use with a single-strand exonuclease that hydrolyses primers to dNTPs, to omit the need of further clean-up before direct DNA sequencing of PCR products, or 3) dephosphorylation of DNA ends for subsequent labelling with $^{32}P$ using $[\gamma\text{-}^{32}P]$ NTP and T4 polynucleotide kinase. The described ALP enzyme reactions are intermediate steps in DNA analysis processes. Other important applications known in the art include those where the enzyme activities are used as reporters such as in enzyme-linked immunosorbent assay (ELISA), in gene-fusion or gene-delivery systems, or in conjugation to oligonucleotides used as hybridisation probes.

Three main ALPs are used in commercially available products;
  i) calf intestinal alkaline phosphatase (CIAP)
  ii) shrimp alkaline phosphatase (SAP) from the arctic shrimp *Pandalus borealis*
  iii) bacterial alkaline phosphatase (BAP)

The animal CIAP and SAP enzymes have similar specific activities of 2000-4000 units/mg protein compared to 50 units/mg BAP protein, which make the two former enzymes more attractive as efficient enzymes. The SAP enzyme is inactivated by moderate heat as discussed below, and is thus preferred for several applications in which the enzyme activity needs to be removed prior to further steps in the processes.

A genetically engineered temperature sensitive BAP mutant was reported [Shandilya, H. And Chatterjee, D. K., 1995. An engineered thermosensitive alkaline phosphatase for dephosphorylating DNA. Focus, 17 (3): 93-95] with no details given to describe the engineering. This mutant enzyme (TsAP), sold by LifeTechnologies, Inc., is inactivated (95% or more) by heat (65° C. for 15 min) in the presence of EDTA only. The recommended reaction temperature for the mutant and the wild-type enzyme is also 65° C. TsAP has at least 40-fold higher activity than wild-type BAP. With reference to high specific activity, TsAP is almost comparable to other ALPs such as CIAP and SAP.

Two heat-labile ALPs from a psycrophilic microorganism have been purified and characterised [de Prada, P., and Brenchley, J. E., 1997, Purification and characterization of two extracellular alkaline phosphatases from a psycrophilic *Arthrobacter* isolate, Appl. Env. Microbiol., 63(7): 2928-2931]. The enzymes that varied with respect to substrate specificities and kinetic properties, displayed different heat-labilities of which the most labile resembles the SAP enzyme lability. No specific activity in units/mg protein and no primary structures were reported.

A cold-adapted ALP from atlantic cod was isolated and characterised [Ásgeirsson, B., Hartemink, R., and Chlebowski, J. F., 1995, Alkaline phosphatase from atlantic cod (*Gadus morhua*). Kinetic and structural properties which indicate adaption to low temperatures. Comp. Biochem. Physiol., 110B(2): 315-329]. The enzyme showed thermolability similar to SAP. No primary structure of the protein/gene was provided.

A study on ALP isozymes from trout [Whitmore, D. H., and Goldberg, E., 1972, Trout intestinal alkaline phosphatases II. The effect of temperature upon enzymatic activity in vitro and in vivo. J. Exp. Zool., 182: 59-68] showed that temperatures of the environment affects the isozyme pattern, and that some isoforms are thermolabile.

Shrimps from the warm water region outside Taiwan contain several ALPs [Lee, A.-C., and Chuang, N.-N., 1991, Charaterization of different molecular forms of alkaline phosphatase in the hepatopancreas from shrimp *Penaeus monodon* (Crustacea: Depacoda). Comp. Biochem. Physiol., 99B(4): 845-850], and the enzymes were concluded to be heat-stable. No primary structures were provided.

An alkaline phosphatase activity from the hepatopancreas of arctic shrimp *Pandalus borealis* was found to be contained in the processing wastewater from the shrimp industry [Olsen, R. L., Johansen, A., and *Myrnes, B.,* 1990, Recovery of enzymes from shrimp waste. Process Biochem. 25:67-68], and the enzyme was later purified from the hepatopancreas [Olsen, R. L., Øverbø, K., and Myrnes, B., 1991, Alkaline phosphatase from hepatopancreas of shrimp (*Pandalus borealis*): a dimeric enzyme with catalytically active subunits. Comp. Biochem. Physiol. 99B(4):755-761]. This purified protein had an apparent molecular weight of 65 kDa (each subunit) and was shown to be a dimeric enzyme with catalytically active subunits in contrast to most other animal ALPs that require dimerisation for activity. According to the report SAP has an isoelectric point of 3.7. The shrimp enzyme efficiently removes terminal 5' phosphate from any DNA strand termini (5' and 3' overhang or blunt ends) produced by restriction endonucleases, although 5' protruding ends are more reactive than blunt ends or 5' recessive ends.

Relative to CIAP, the SAP enzyme has a slight shift to lower temperatures for activity, but it is not considered to be truly cold-active. With a maximum enzyme activity at about 40° C. (45° C. for CIAP), almost 40% activity is retained at 10° C. or at 50° C. compared to 10% and 90% activity, respectively, for CIAP. Although the temperature for maximum activity is close to 40° C., the SAP enzyme starts to loose activity when pre-incubated for a period of 15 min beyond 37° C. After pre-incubation at 65° C. the SAP activity is reduced by 95% or more and the activity is undetectable after pre-incubation at 70° C. In comparison, after similar heat-treatments CIAP retains 40% and 20% of its activity.

Thus, relative to its commercial competitor, the SAP enzyme is heat-labile and cold-active making it particularly suited for use in multi-step laboratory protocols where a simple heating step can de-activate the enzyme so that it plays no part in further method steps.

BIOTEC ASA, Tromsø, Norway, produces the commercial SAP enzyme, from the shrimp industry wastewater. Onboard the trawlers, freshly collected shrimps are frozen in large blocks. When landed the shrimps are carefully thawed by re-circulated cold water. Approximately 1000 l of water is used for 4000 kg of shrimp. During the process of freezing and thawing, the shrimp hepatopancreas breaks and the contents are released to the water. This wastewater is then concentrated and several chromatographic steps are used to purify the SAP enzyme.

The producer supplies SAP for the world market through well-known companies like USB, Boehringer-Mannheim or Amersham Pharmacia Biotech.

Due to its high specific activity, its "versatility" regarding DNA termini, and its relative temperature-lability, SAP is frequently used in dephosphorylation of cloning vectors prior to ligation reactions, and in treatment of PCR amplification product-mixtures prior to DNA sequencing reactions as described in U.S. Pat. Nos. 5,741,676 and 5,756,285.

The present production of SAP suffers from varying quality of the wastewater, which again affects the production efficiency. Two factors cause this variation; i) natural seasonal variation of enzyme production in the shrimp; and ii) the handling of the shrimp source prior to or during freezing and the handling of shrimps or water during or after the thawing process.

There is also a concern about the future availability of wastewater; i) as a natural resource shrimps are not guaranteed to be available at all times; and ii) the shrimp industry is now looking into possible new ways to freeze the shrimps, i.e. single-freezing, from which the wastewater has been tested to contain small amounts of enzymes such as SAP.

In addition to these practical problems, the market has a demand for a recombinant SAP product as recombinant products are frequently preferred in molecular biology techniques, particularly where product purity is an issue, e.g. in the production of DNA based therapeutics or in forensic science. SAP has highly advantageous enzymatic and physiochemical properties and is a preferred enzyme for the laboratory protocols in which it is useful. There is therefore an appreciable need for a synthetic or recombinant source of SAP, which is produced in a uniform and pure fashion. However, neither DNA or amino acid sequences for SAP have been previously elucidated.

In order to isolate the gene and to subsequently clone and produce a recombinant SAP, several attempts have been made to obtain an N-terminal sequence of the purified protein. None of these attempts have succeeded. The sequence analyses have revealed multiple (four or more) alternative amino acids for each specific N-terminal position. Thus, no protein sequence information has been available for use, even with highly degenerate oligonucleotide probes, to hunt for the SAP gene. The reason(s) for the non-homologous N-termini in an apparently homogenous enzyme preparation can only be speculated. It is possible that SAP isoforms are produced by different genes, by alternative splicing or by varying post-translational modifications of the protein, or that SAP is attacked by proteases at the N-terminus with no detectable reduction in molecular weight.

It has also been found by the present inventors that the limited homology between the alkaline phosphatase from the hepatopancreas of arctic shrimps (*Pandalus borealis*) and alkaline phosphatase from species which have been sequenced prevents the routine isolation of nucleic acid sequences encoding alkaline phosphatase from *Pandalus borealis*.

BRIEF SUMMARY OF THE INVENTION

In spite of these real difficulties in obtaining a coherent consensus amino acid sequence for SAP, the Inventors have surprisingly been able to isolate a cDNA encoding SAP from a *Pandalus borealis* cDNA library and thus elucidate the coding sequence for SAP. The invention relates to the provision of an SAP cDNA and its use in providing an alternative source of the enzyme.

The sequence of SEQ ID No. 1 corresponds to the full cDNA sequence of the enzyme minus a small portion at the 5' end. Nevertheless, the expression product of a nucleic acid molecule comprising this sequence is believed to have all or at least a significant proportion (i.e. at least 60%, 70%, 80% or typically at least 90%) of the activity of the native enzyme. The few N-terminal amino acids missing from this sequence do not contain binding sites for the substrate or of actor.

Hence reference herein to SAP or to a heat labile alkaline phosphatase is taken to also include molecules which are smaller than naturally occurring ALPs but have the same or substantially the same activity. Advantageously, such expression products and other recombinant ALP enzymes according to the invention may have a greater activity than the native enzyme as isolated. Preferably the specific activity is higher than the published value for SAP of 1900 U $mg^{-1}$. A suitable test for enzymatic activity is described herein [Olsen et al.].

Thus in one aspect, the present invention provides a (an isolated) nucleic acid molecule comprising (preferably consisting essentially of) a nucleotide sequence as set forth in SEQ ID No. 1 or having at least 55% sequence identity therewith and/or capable of hybridising under medium stringency conditions to the complementary sequence of SEQ ID No. 1, or the complementary sequence of said sequences, wherein said nucleotide sequence encodes or is complementary to a sequence which encodes a heat labile alkaline phosphatase.

A nucleic acid molecule according to the invention may thus be single or double stranded DNA, cDNA or RNA.

A nucleic acid molecule of the invention may be an isolated nucleic acid molecule (in other words isolated or separated from the components with which it is normally found in nature) or it may be a recombinant or a synthetic nucleic acid molecule.

Reference is made herein to sequences consisting essentially of the sequence of SEQ ID No. 1 and its variants. Thus flanking regions at either end may also be present. In particular, a 5' flanking region may be present of 1 to 81 or 1-60 nucleotides, more particularly 1-30 nucleotides, which may incorporated signalling sequence for directing processing of the active mature form of the enzyme during transcription/translation. 3' flanking regions will typically contain 1-60, e.g 1-30 additional nucleotides.

The complement of a given sequence will be a single precise sequence which can be determined according to the normal rules of base pairing.

Preferably the above nucleotide sequence will have at least 65%, more preferably at least 75%, e.g. at least 85% or at least 95% sequence identity with SEQ ID No. 1 or its complement. Likewise, the nucleotide sequence will preferably hybridise under high stringency conditions to SEQ ID No. 1 or its complement. While the present invention is based on the identification of the amino acid sequence and cDNA sequence for SAP, it is well understood in the art that variants of these sequences, e.g. allelic variants and related sequences modified by single or multiple base substitution, addition or deletion will exist or can be generated which are functionally equivalent to the newly identified sequences.

A particularly preferred embodiment of the present invention is an isolated nucleic acid molecule which encodes a thermolabile eukaryotic alkaline phosphatase, preferably such an enzyme derived from shrimp, and derivatives of such enzymes. These derivatives may incorporate conservative amino acid substitutions, in that amino acids from the naturally occurring enzyme may be replaced by amino acids having similar functional characteristics in terms, e.g. of size, lipophilicity and polarity. Such functionally related groups of amino acids being understood by the man skilled in the art. Further additions, deletions or substitutions may also be included which do not significantly affect the enzyme's catalytic activity. Typically the enzyme derivatives will have 1-50, preferably 1-30, e.g 1-15 non-conservative alterations as compared to the native enzyme.

By "functionally equivalent" is meant nucleic acid sequences which encode polypeptides (or polypeptides themselves) having alkaline phosphatase activity, preferably of similar or greater specific activity compared to the native enzyme isolated from *Pandalus borealis* processing wastewater. In other words, functionally equivalent nucleic acid sequences encode polypeptides which can catalyse the removal of terminal 5' phosphate groups from DNA strand terminii (5' and 3' overhang or blunt ends) produced, for example by restriction endonucleases.

Variations in the alkaline phosphatase-encoding nucleotide sequence may occur between different populations of *Pandalus borealis* within the species, between similar populations of different geographical origin, and also within the same organism. Such variations are included within the scope of this invention.

For the purposes of defining the level of stringency, a medium stringency comprises a hybridisation and/or a wash carried out in 0.2×SSC-2×SSC buffer, 0.1% (w/v) SDS at 42° C. to 65° C., while a high stringency comprises a hybridisation and/or a wash carried out in 0.1×SSC-0.2×SSC buffer, 0.1 (w/v) SDS at a temperature of at least 55° C. Conditions for hybridisations and washes are well understood by one normally skilled in the art.

Included within the scope of the invention are nucleotide sequences which hybridise to SEQ ID NO. 1 or its complement, or to parts thereof (i.e. to hybridisation probes derived from SEQ ID NO. 1), under high stringency conditions and which preferably encode or are complementary to a sequence which encodes an alkaline phosphatase enzyme or part thereof. Conditions of high stringency may readily be determined according to techniques well known in the art, as described for example in Sambrook et al., 1989, Molecular Cloning, A Laboratory Manual, 2nd Edition. Hybridising sequences included within the scope of the invention are those binding under non-stringent conditions (6×SSC/50% formamide at room temperature) and washed under conditions of high stringency (e.g. 0.1×SSC, 68° C.), where SSC=0.15 M NaCl, 0.015M sodium citrate, pH 7.2.

A hybridisation probe may be a part of the SEQ ID No. 1 sequence (or complementary sequence), which is of sufficient base length and composition to function to hybridise to sample or test nucleic acid sequences to determine whether or not hybridisation under high stringency condition occurs. The probe may thus be at least 15 bases in length preferably at least 30, 40, 50, 75, 100 or 200 bases in length. Representative probe lengths thus include 30-500 bases e.g. 30-300, 50-200, 50-150, 75-100.

Nucleotide sequence identity may be determined using the BestFit program of the Genetics Computer Group (GCG) Version 10 Software package from the University of Wisconsin. The program uses the local homology algorithm of Smith and Waterman with the default values:

Gap creation penalty=50, Gap extension penalty=3, Average match=10,000, Average mismatch=−9.000.

Methods for producing variants of the specific sequences set out herein, for example by site-directed mutagenesis, random mutagenesis, or enzymatic cleavage and/or ligation of nucleic acids are well known in the art, as are methods for determining whether the thus-modified nucleic acid has significant homology to the subject sequence, for example by hybridisation.

Alternatively viewed, the present invention provides an isolated nucleic acid molecule which encodes or is complementary to a sequence which encodes a heat labile alkaline phosphatase, said alkaline phosphatase comprising the amino acid sequence of SEQ ID No. 2 or variants of said amino acid sequence which are at least 50%, preferably at least 60% e.g. at least 70% or 80% identical thereto.

The invention also provides a cDNA, preferably derived from *Pandalus borealis*, encoding a heat labile alkaline phosphatase comprising the amino acid sequence of FIG. 2 (SEQ ID NO. 2) or a variant or fragment thereof being heat labile and having alkaline phosphatase activity.

The invention also provides a cDNA, preferably derived from *Pandalus borealis*, encoding a heat labile alkaline phosphatase consisting of an amino acid sequence of which one or more amino acid residues are deleted from, substituted for, or added to the amino acid sequence of SEQ ID NO. 2.

A further aspect of the invention provides a polypeptide encoded by a nucleic acid molecule of the invention as defined herein. Provision of a nucleic acid molecule according to the invention thus enables recombinant alkaline phosphatase enzymes particularly SAP and variants thereof to be obtained in quantities and with a purity previously unavailable, thereby permitting a sustainable supply of the enzyme in a form that can be manufactured wholly under controlled conditions or according to certifiable conditions as specified at any time.

Accordingly, the present invention also extends to recombinant polypeptides comprising (or consisting essentially of) an amino acid sequence constituting a heat labile alkaline phosphatase enzyme encoded by the nucleotide sequence as shown in FIG. 1 (SEQ ID No. 1), or a functionally-equivalent variant thereof. Alternatively viewed, the invention also provides recombinant polypeptides comprising an amino acid sequence constituting a heat labile alkaline phosphatase enzyme, encoded by the nucleotide sequences as shown in FIG. 1 (SEQ ID No. 1), or a functionally-equivalent variant thereof, substantially free from other *Pandalus borealis* components.

The term "polypeptide" as used herein includes both full length protein, and shorter peptide sequences.

"Functionally equivalent" as used above in relation to the polypeptide amino acid sequences defines polypeptides related to or derived from the above-mentioned polypeptide sequences where the amino acid sequence has been modified by single or multiple amino acid substitution, addition or deletion, and also sequences where the amino acids have been chemically modified, including by glycosylation or deglycosylation, but which nonetheless retain catalytic activity. Such functionally-equivalent variants may occur as natural biological variations or may be prepared using known techniques, for example functionally equivalent recombinant polypeptides may be prepared using the known techniques of site-directed mutagenesis, random mutagenesis, or enzymatic cleavage and/or ligation of amino acids.

The synthetic polypeptides according to this aspect of the invention may be prepared by expression in a host cell containing a recombinant DNA molecule which comprises a nucleotide sequence as broadly described above operatively linked to an expression control sequence, or a recombinant DNA cloning vehicle or vector containing such a recombinant DNA molecule e.g. a plasmid, cosmid, bacteriophage molecule or yeast artificial chromosome. Alternatively the polypeptides may be expressed by direct injection of a naked DNA molecule according to the invention into a host cell.

The synthetic polypeptide so expressed may be a fusion polypeptide comprising a catalytically functional portion of an alkaline phosphatase enzyme and an additional polypeptide coded for by the DNA of the recombinant molecule fused thereto. For example, it may be desirable to produce a fusion protein comprising a synthetic alkaline phosphatase or other polypeptide according to the invention coupled to a protein such as β-galactosidase, phosphatase, glutathione-S-transferase, urease and the like. Most fusion proteins are formed by expression of a recombinant gene in which two coding sequences have been joined together with reading frames in phase. It may also be desirable to fuse synthetic peptides of the invention to proteins or peptides with a ligand binding function, for example antibodies, to produce, for example enzyme-linked reporter antibodies, as well known in the art. All such fusion or hybrid derivatives of alkaline phosphatase-encoding nucleic acid molecules and their respective amino acid sequences are encompassed by the present invention. Such suitable recombinant DNA and polypeptide expression techniques are described for example in Sambrook et al., 1989.

Alternatively, the polypeptides of the invention may be produced by chemical means, such as the well-known Merrifield solid phase synthesis procedure.

More particularly, this aspect of the invention provides a recombinant polypeptide comprising (or consisting essentially of):

(a) all or part of an amino acid sequence as shown in SEQ ID No. 2; or
(b) all or part of an amino acid sequence which has at least 60% sequence identity with all or part of SEQ ID No. 2.

The term 'recombinant' distinguishes these molecules from naturally occurring polypeptides and signifies that the molecule has been generated using 'recombinant DNA technology', a phrase well understood in the art. The enzyme having the amino acid sequence of SEQ ID No. 2 is believed to be a truncated version of the naturally occurring enzyme in *Pandalus borealis* and therefore if the corresponding nucleic acid is used in recombinant production then the produced recombinant enzyme will in any event not be the same as the non-recombinant naturally produced molecule.

In particular the amino acid sequence may exhibit at least 65%, 70%, 75%, 80%, 85%, 90%, 95% or 98% identity with the polypeptide of SEQ ID No. 2. Alternatively, the amino acid sequence may exhibit at least 70%, 75%, 80%, 85%, 90%, 95% or 98% similarity with the polypeptide of SEQ ID No. 2.

In particular variations may occur at the N terminus. The polypeptides of the invention may also include a further 4-20, e.g 5-10 amino acids at the N terminus. It should also be noted that the incomplete cDNA sequence of SEQ ID NO. 1 corresponds to the amino acid sequence of SEQ ID NO. 2 but begins only at residue 7, aspartic acid. In the recombinant polypeptide, amino acid variations, in particular substitutions, may occur within these first 6 amino acids as compared to the sequence given in FIG. 2. Furthermore, the N terminal lysine residue of FIG. 2 may be replaced by arginine.

A cDNA sequence corresponding to the amino acid sequence of SEQ ID No. 2 can be generated and this is made up of SEQ ID No. 1 together with the derived nucleotide sequence at the 5'end. This region is also, for the most part, provided by the forward primer of SEQ ID No. 7, itself derived from a sequenced fragment of native SAP. Due to the degeneracy of the genetic code, it is not possible from the amino acids KAYWNK (SEQ ID NO: 26) to specify the sequence more precisely than AArGCnTAyTGGAAyAAr [SEQ ID No. 19] wherein r=A or G, n=T, C, A or G and y=C or T. The full cDNA sequence corresponding to SEQ ID No. 2 which comprises SEQ ID No. 19 and SEQ ID No. 1 is referred to herein as SEQ ID No. 20.

However, the sequencing work carried out as part of Example 4 has established the full cDNA sequence for Pandalus borealis alkaline phosphatase. Thus the uncertainties discussed above in respect of SEQ ID No. 19 have been resolved and the cDNA encoding KAYWNK (SEQ ID NO: 26) is as follows: AAAGCATATTGGAACAAA [SEQ ID No. 21]. This sequence can replace SEQ ID No. 19 within SEQ ID No. 15 to produce, together with the part of SEQ ID No. 17 encoding the amino acid sequence NPITEED (SEQ ID NO: 27), the precise cDNA sequence encoding the recombinant enzyme. This full sequence is referred to as SEQ ID No. 22.

Amino acid sequence identity or similarity may be determined using the BestFit program of the Genetics Computer Group (GCG) Version 10 Software package from the University of Wisconsin. The program uses the local homology algorithm of Smith and Waterman with the default values: Gap creation penalty=8, Gap extension penalty=2, Average match=2.912, Average mismatch=−2.003.

A "part" of the amino acid sequence of SEQ ID No. 2 or its variants as defined above may comprise at least 20 contiguous amino acids, preferably at least 30, 40, 50, 70, 100, 150, 200, 300, 400 or 450 contiguous amino acids. Parts having above 200, particularly above 300 amino acids can be considered 'significant parts' and such parts will typically have the enzymatic active site as identified herein and preferably the co-factor binding site.

The recombinant polypeptide is preferably functionally active according to the definitions given above, e.g. is enzymatically active. Alternatively, it may not itself be functionally active but may provide regions with functional properties of the whole, e.g. represent the active site or co-factor binding site required for enzymatic activity.

As discussed above, SEQ ID No. 1 and SEQ ID No. 2 do not correspond to the complete cDNA or amino acid sequence of the native SAP. The truncated polypeptides which exhibit the same or substantially the same enzymatic activity as native SAP and retain that enzyme's thermolability constitute a further aspect of the present invention. The complete cDNA molecules or recombinant polypeptides which incorporate the truncated sequences defined herein or functionally equivalent variants thereof comprise further preferred aspects of the present invention.

According to a further aspect of the present invention is provided a polypeptide having the same or substantially the same catalytic activity and thermal properties as SAP but lacking part of its N-terminal region. Preferably, these polypeptides lack the N terminal amino acid and 2-50, preferably 5-30 e.g. 5-10 amino acids which are adjacent thereto in the native enzyme. By 'substantially the same catalytic activity' is meant that the polypeptide has at least 75%, preferably at least 85%, more preferably at least 90% of the activity of native SAP. Apart from these missing N-terminal parts, the polypeptides preferably have at least 60%, 65%, 70%, 75%, 80%, 85%, 90%, 95% or 98% identity with the polypeptide of SEQ ID No. 2.

According to the present invention, an alkaline phosphatase can be considered heat labile if its catalytic activity is undectable after pre-incubation at 65° C. for 15, preferably 10 minutes.

A suitable assay for the catalytic activity of enzymes of the invention follows that of Olsen et al. [R. L. Olsen, K. Øverbø, and B. Myrnes (1991) Alkaline phosphatase from the hepatopancreas of shrimp (Pandalus borealis): a dimeric enzyme with catalytically active subunits, Comp. Biochem. Physiol., 998: 755-761]. Alkaline phosphatase activity is determined by incubating enzyme with 6 mM p-nitrophenyl phosphate at 37° C. in 0.1 M glycine/NaOH buffer pH 10.4 with 1 mM $MgCl_2$, and 1 mM $ZnCl_2$ in a total volume of 0.5 ml. After 15 min, the reaction is stopped by 0.5 ml of 2M NaOH and the amount of p-nitrophenol released is determined by measuring the absorbance at 405 nm ($\epsilon_{405}$=18.5 $mM^{-1}$ $cm^{-1}$). One unit of enzyme activity will produce 1 μmol of p-nitrophenol per min. SAP is not negatively affected by zinc, and there is no significant demand of magnesium above a minimal concentration.

Also envisaged within the scope of the invention are variants of SEQ ID. No. 1 or SEQ ID. No. 2 which encode or comprise proteins which retain and exhibit the catalytic properties of SAP, but which are thermostable—i.e. do not suffer from complete loss of activity after heating at 70° C. for 15 min.

Also provided are methods for preparing recombinant nucleic acid molecules according to the invention, comprising inserting the nucleic acid molecules containing the nucleotide sequences of the invention into another nucleic acid molecule, e.g. into vector nucleic acid, e.g. vector DNA.

Thus the invention further provides a recombinant vector, which is a vector DNA possessing a DNA fragment comprising any one of cDNAs of the invention.

In the recombinant vector, the vector DNA is preferably an expression vector, and is capable of propagation in a host cell such as *Escherichia coli*, *Saccharomyces cerevisiae* or *Pichia pastoris*.

Expression vectors of the invention may include appropriate control sequences such as for example translational (e.g. start and stop codons, ribosomal binding sites) and transcriptional control elements (e.g. promoter-operator regions, termination stop sequences) linked in matching reading frame with the nucleic acid molecules of the invention.

Vectors according to the invention may include plasmids and viruses (including both bacteriophage and eukaryotic viruses) according to techniques well known and documented in the art, and may be expressed in a variety of different expression systems, also well known and documented in the art.

A variety of techniques are known and may be used to introduce such vectors into prokaryotic or eukaryotic cells for expression, or into germ line or somatic cells to form transgenic animals. Suitable transformation or transfection techniques are well described in the literature.

A genetic construct comprising a nucleic acid molecule of the invention as defined herein operably linked to a promoter sequence constitutes a further aspect of the present invention.

The invention also includes transformed or transfected prokaryotic or eukaryotic host cells, or transgenic organisms containing a nucleic acid molecule according to the invention as defined above. For convenience, herein, no distinction is made between transformation and transfection. Such host cells may for example include prokaryotic cells such as *E. coli, Streptomyces* and other bacteria, eukaryotic cells such as yeasts (e.g. *Pichia pastoris*) or the baculovirus-insect cell system, transformed mammalian cells and transgenic animals and plants. Prokaryotic host cells being preferred.

Thus the invention also provides a transformant, which is a cell transformed with the recombinant vector of the invention.

In a further aspect, the present invention provides a recombinant cell or organism having a nucleic acid molecule comprising a nucleotide sequence as set forth in SEQ ID Nos. 1 or 20, or a functionally equivalent variant thereof as defined herein, and which expresses or is capable of expressing a thermolabile alkaline phosphatase. The cell or organism is 'recombinant' in that it contains genetic material (in this case encoding a thermolabile alkaline phosphatase) which is not native to that organism, thus the shrimp *Pandalus borealis* is excluded, for while it expresses a thermolabile alkaline phosphatase, the gene therefore is found naturally in that species.

Alternatively viewed, the cell or organism expressing a thermolabile alkaline phosphatase could be considered "modified" in that such a cell or organism of that genotype and phenotype does not exist naturally. Thus the cell or organism could also be termed a "non-naturally" occurring cell or organism due to the presence in it of non-native genetic material and its ability to produce a protein (a thermolabile alkaline phosphatase) not produced by naturally occurring members of that species or cell type.

The above described cells and organisms can be termed transformants in that they or their ancestors have been transformed by introduction of genetic material encoding a thermolabile alkaline phosphatase as described herein.

The invention also provides another transformant, which is *Escherichia coli* or *Saccharomyces cerevisiae* transformed with the recombinant-vector. Suitable expression strains of bacteria, yeasts and other cultured cells are known in the art.

The invention also provides a process for producing a heat labile alkaline phosphatase, comprising culturing the transformants of the invention in a culture medium and isolating the alkaline phosphatase from the cultured transformant. More particularly, the invention provides a method for the manufacture of a heat labile alkaline phosphatase, comprising transforming a host cell with an expression vector that comprises a nucleotide sequence as set forth in SEQ ID Nos. 1 or 20 or having at least 55% sequence identity therewith and/or capable of hybridising under medium stringency conditions to the complementary sequence of SEQ ID Nos. 1 or 20, or the complementary sequence of said sequences, maintaining the cell in a culture medium and isolating heat labile alkaline phosphatase expressed by said cell. Methods of cell culturing are well known in the art and will typically allow for cell multiplication and simultaneous or subsequent expression of the ALP gene. The gene product may accumulate intracellularly or extracellularly. Methods for harvesting and purifying proteins generated in this way are well known in the art.

Further work has been done and the precise sequence information refined. The changes in the revised cDNA and protein sequences are minor. The revised cDNA sequence is shown in FIG. 4 and called SEQ ID No. 15. As well as incorporating an additional 5' sequence (the equivalent amino acid sequence of which was always present in SEQ ID No. 2) it lacks 9 nucleotides as shown in the comparison of sequences in FIG. 7. As compared the sequences are 99.4% identical.

On the protein level, there is a slightly bigger change as the corrections created a change in the reading frame in a small part of the protein. The revised amino acid sequence is shown in FIG. 5 and is called SEQ ID No. 16. A comparison with the original amino acid sequence is shown in FIG. 8. As compared the sequences are around 96% identical.

Thus, all references hereinbefore to SEQ ID Nos. 1 and 2 may be replaced with SEQ ID Nos. 15 and 16 respectively. These sequences comprising preferred embodiments of the invention already described.

In addition, a sequence for the full cDNA of SAP has recently been elucidated and thus the whole molecule corresponds to SEQ ID No. 17 followed by SEQ ID No. 15 and the full amino acid sequence of SAP (plus signal sequence) corresponds to SEQ ID No. 18 followed by SEQ ID No. 2 or 16. It is believed that of the 47 amino acids of SEQ ID No. 18, the last 7 amino acids (NPITEED) (SEQ ID NO: 27) or some of them, e. g. PITEED (SEQ ID NO: 28) or TEED (SEQ ID NO: 29) are found at the N terminus of the mature SAP protein. The remaining amino acids are thought to be a signal polypeptide. Molecules having these sequences constitute further aspects of the present invention. In a preferred embodiment of the present invention the recombinant alkaline phosphatases have the amino acid sequence NPITEED (SEQ ID NO: 27) at their N terminus.

BRIEF DESCRIPTION OF THE SEVERAL VIEWS OF THE DRAWINGS

FIG. 1 shows the cDNA sequence encoding SAP from *Pandalus borealis* (minus a small portion at the 5' end). The stop codon and the cDNA downstream sequence including the polyA tail are underlined;

FIG. 2 shows the amino acid sequence encoded by the SAP cDNA shown in FIG. 1 (and incorporates an additional N terminal region). Homologies to sequenced protein fragments are underlined and specified. The sequence of the enzyme active site (according to known alkaline phosphatases) is shown in bold type; and FIG. 3 shows the SAP sequence (SAP: SEQ ID NO: 1) aligned to its top scoring homologs of tissue-nonspecific ALPs found in the Swiss-Prot database; mouse (Accession number P09242: SEQ ID NO:30), human (A. n. P05186: SEQ ID NO:31), chicken (A. N. Q92058: SEQ ID NO:32) and an ALP of the silk moth Bombyx mon (A.n. P29523: SEQ ID NO:33). The conserved consensus seciuence is shown below the alignment (SEQ ID NO:34).

FIG. 4 shows the revised DNA sequence encoding SAP form *Pandalus borealis* (SEQ ID NO:15). The polyA-tail is indicated $(A)_{23}$. Five nucleotide positions in the 5'-sequence (lower case) are biased by the degenerated PCR primer used for amplification and sequencing, and the positions are thus not specified.

FIG. 5 shows the amino acid sequence encoded by the SAP cDNA shown in FIG. 4 (SEQ ID NO: 16). Homologies to sequences protein fragments are underlined and specified. The sequence of the proposed enzyme active site is shown in bold. The N-terminal lysine residue (lower case) could alternatively be arginine because of the biasing of degenerated PCR primer as discussed in respect of FIG. 4 above.

Figure 6:
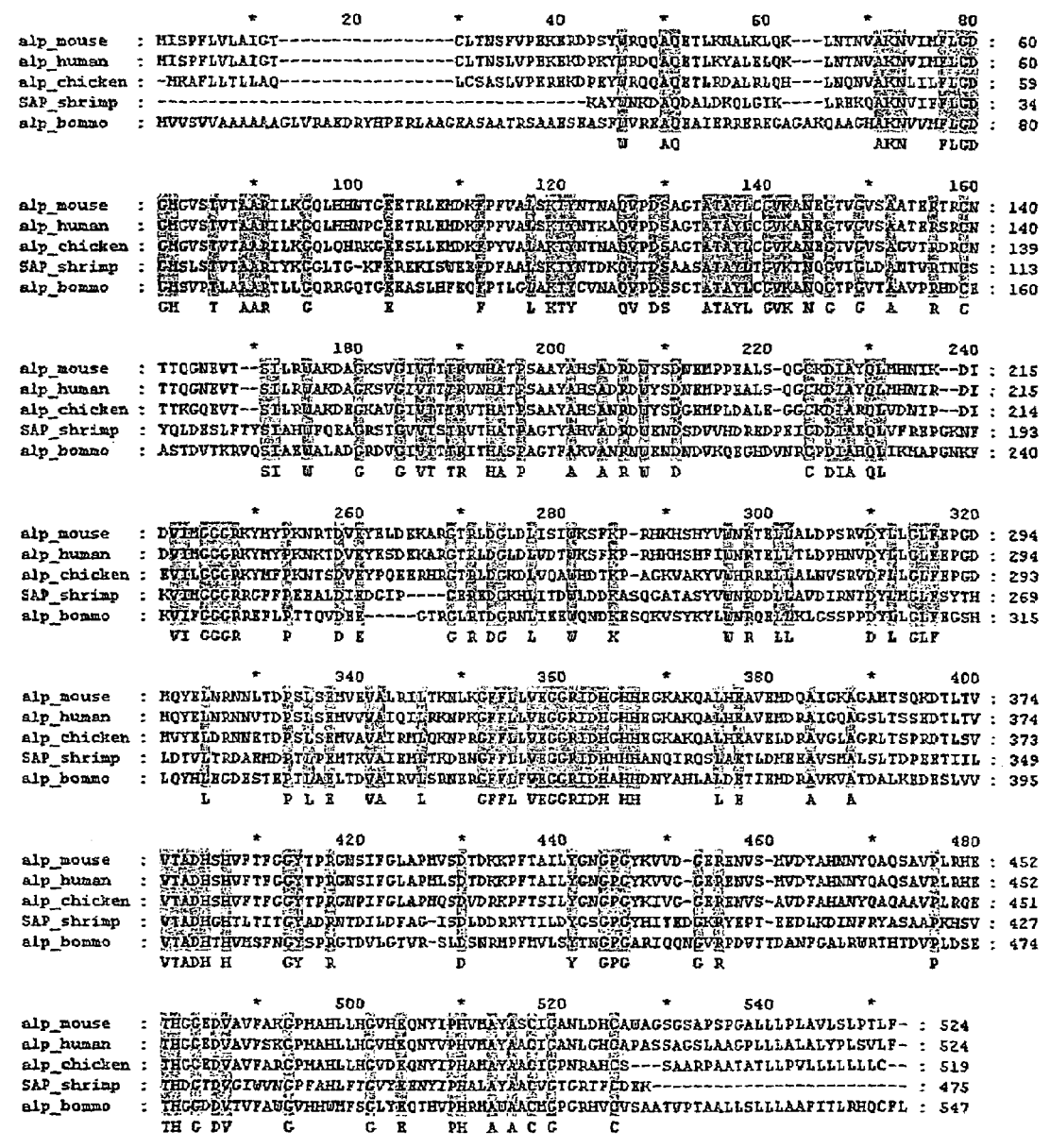

FIG. 6 corresponds to FIG. 3 above but incorporates that revised amino acid sequence of FIG. 5 (SEQ ID NOS: 16 and 30-33). The conserved consensus sequence is shown below the alignment (SEQ ID NO:35).

FIG. 7 shows an alignment of the revised cDNA sequence of FIG. 4 (top; SEQ ID NO:15) with the original sequence of FIG. 1 (SEQ ID NO: 1; additionally comprising the 5' end originally only presented in the equivalent amino acid sequence of FIG. 2). The comparison was performed using the Needle program which used the Needleman-Wunsch global alignment algorithm to find the optimal alignment (including gaps) of two sequences. [Needleman et al. J. Mol. Biol. (1983) 48, pp 443-453], matrix Blosum 62 with gap penalties of Gap open=10.0 and Gap extend=0.5. The overall % identity=96.03.

FIG. 8 shows an alignment of the revised amino acid sequence of FIG. 5 (top; SEQ ID NO:16) with the original amino acid sequence of FIG. 2 (SEQ ID NO:2). The comparison was performed using the above-described Needle program, matrix Blosum 62 with gap penalties of Gap open=10.0 and Gap extended=0.5. The overall % identity=96.03.

DETAILED DESCRIPTION OF THE INVENTION

EXAMPLES

Example 1

Figures 9, 10:
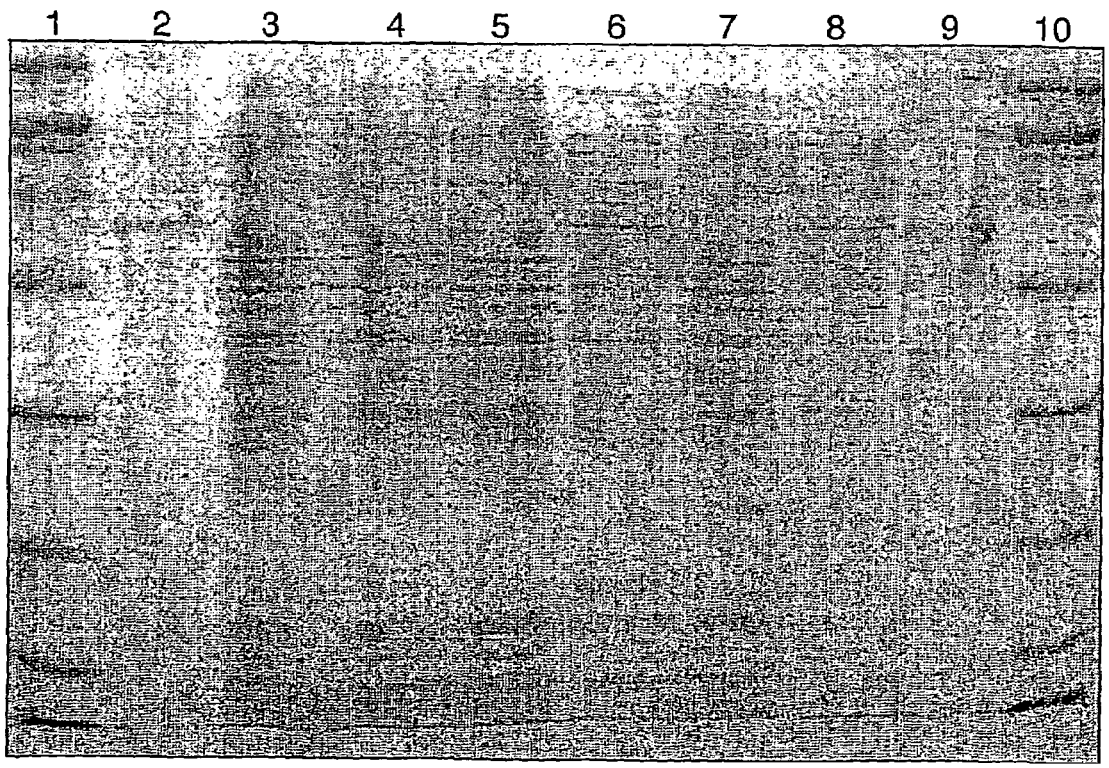
FIG. 9 gives the cDNA (SEQ ID NO.:17) and amino acid (SEQ ID NO.:18) sequence of the proposed signal sequence and N-terminal region of alkaline phosphatase from *Pandalus borealis*. The SAP amino acid sequence continues then with KAYWNK (SEQ ID NO:26) . . . as described in FIGS. 2 and 4.
FIG. 10 is a photo from an SDS-PAGE of total cell protein extracts from the expression cultures of Example 4, in which: Lane 1 and 10: Broad Range protein standard, Lane 2 and 9: SAP 1.5 µg, Lane 3: negative control culture, non induced, Lane 4: negative control culture, induced, Lane 5: SAP-culture 1, non-induced, Lane 6: SAP-culture 1, induced, Lane 7: SAP-culture 2, non-induced, Lane 8: SAP-culture 2, induced. The proteins in the Broad-Range protein standard are: myosine (200 kD), β-galactosidase (116 kD), phosphorylase b (97.4 kD), serum albumin (66 kD), ovalbumine (45 kD), carbonic anhydrase (31 kD), trypsin inhibitor (21.5 kD), lysozyme (14.4 kD) and aprotinin (6.5 kD).

Sequencing the Sap Protein and Isolating the Sap Gene

Protein Isolation, Fragmentation and Sequence Analysis

Shrimp alkaline phosphatase (SAP) was purified to apparent homogeneity as described [R. Olsen et al., 1991]. A single protein band of approximately 55 kDa was detected by coomassie as well as silver staining after electrophoresis in 10% NuPAGE Bis-Tris gel system (Novex) using a 50 mM 2-(N-morpholino) ethane sulphonic acid running buffer containing 0.1% SDS.

1 mg protein was lyophilised and submitted to a commercial sequence analysis service (Innovagen, Sweden) where the protein was fragmented by trypsin and the fragments were separated by reverse-phase HPLC. More than 30 fragments were produced and 4 fragments were selected for further analysis. Mass spectrometry mediated sequence analysis of the selected fragments (H23:18, H23:30, 5ReRP6:26, 5ReRP6:17) produced 12, 10, 8 and 5 amino acids in sequence, respectively.

Synthesis of Oligonucleotides Derived from Protein Fragment Sequences

Based on the amino acid sequences, standard codons were predicted and degenerated deoxyribo-oligonucleotides of forward and reverse complementary sequences were subsequently custom made (Eurogentec, Belgium).

Synthesis of Shrimp cDNA

Freshly collected *P. borealis* shrimps were dissected and individual hepatopancreas were stored on liquid nitrogen until use. mRNA was isolated from a single hepatopancreas by the use of PolyATract® System 1000 (Promega). Isolated mRNA was used for first strand cDNA synthesis before second strand synthesis and cDNA amplification was performed following instructions given in the Smart™ PCR cDNA synthesis kit (Clontech) and the Advantage cDNA PCR kit (Clontech).

PCR Amplification and Sequence Analysis of a SAP-Gene Internal Fragment

A small aliquot of the synthesised cDNA was used as template in PCRs primed by pair-wise combinations (forward and reverse directions) of the protein-derived oligonucleotides. The amplification reactions, having standard mixture compositions, were run in an Eppendorf gradient thermocycler. PCR products were detected after agarose gel electrophoresis. The primer combination of oligonucleotides 17F and 26R gave a distinct amplification product of approximately 600 bp which was sequenced using the Thermo Sequenase radiolabelled terminator cycle sequencing kit (Amersham) by exploiting the same PCR primers for sequencing.

Rapid Amplification of cDNA Ends (RACE)

Based on the DNA sequence found in the PCR product, new specific forward and reverse primers for 5' and 3' RACE reactions were synthesised as described for the use with the Marathon™ cDNA amplification kit (Clontech) in amplification from the cDNA template.

By the use of the SAP gene-specific forward primer MalpF in combination with the kit-contained AP1 primer, having sequence identity to the ligated adaptor, a 1.4 kb 3'-RACE fragment was produced. Similarly, the reverse gene-specific primer MalpR gave rise to a 0.5 kb 5'-RACE product. DNA sequencing analysis of the 3'-RACE product confirmed that the RACE product overlapped the 600 bp PCR product. The 3'-RACE product was subcloned into the pCR-Script vector (Stratagene) to produce the pMalpF plasmid for further sequencing of the cDNA gene downstream of the sequence region contained in the 600 bp PCR product.

The 600 bp PCR product and the pMalpF insert were sequenced several times in both directions using new gene specific primers.

High-fidelity PCR Amplification of the Entire cDNA Gene

A final PCR reaction was performed using primers SapF and SapR and the Pfu polymerase (Stratagene) and cDNA as template for a 1.5 kb SAP cDNA gene amplification product. The 1.5 kb PCR product was analysed for confirmation of the obtained sequence. The cDNA gene was found to contain an open reading frame encoding a 478 amino acid polypeptide and a 3' sequence that includes a putative signal for polyadenylation of the transcript—see FIGS. 1 and 2.

Thermal Cycling Profiles used in PCR

The following cycling profiles were used for amplification reactions:

| | | |
|---|---|---|
| total cDNA amplification | 1x: | 95° C., 2 min |
| | 16x: | 95° C., 5 sec |
| | | 65° C., 5 sec |
| | | 68° C., 6 min |
| internal 600 bp fragment PCR | 1x: | 94° C., 2 min |
| | 36x: | 94° C., 10 sec |
| | | 51° C., 10 sec |
| | | 72° C., 1 min |
| | 1x: | 72° C., 5 min |
| 5' RACE | 1x: | 94° C., 30 sec |
| | 5x: | 94° C., 5 sec |
| | | 72° C., 4 min |
| | 1x: | 94° C., 30 sec |
| | 5x: | 94° C., 5 sec |
| | | 70° C., 4 min |
| | 1x: | 94° C., 30 sec |
| | 23x: | 94° C., 5 sec |
| | | 68° C., 4 min |
| 3' RACE | 1x: | 94° C., 30 sec |
| | 36x: | 94° C., 5 sec |
| | | 68° C., 4 min |
| high-fidelity PCR | 1x: | 94° C., 3 min |
| | 40x: | 94° C., 10 sec |
| | | 55° C., 15 sec |
| | | 72° C., 3 min |
| | 1x: | 72° C., 5 min |

Results

The SAP protein subunit was originally estimated to have a molecular mass of 65 kDa. The USB product sheet describes a 59 kDa SAP protein, and in the Inventors' SDS-PAGE system, SAP migrates in a similar fashion to a 55 kDa protein of the molecular weight standard. Discrepancies are probably explained by variations in buffer systems and gel qualities used.

The isolated cDNA encodes a polypeptide having sequence identities to the analysed SAP protein fragments—see FIG. 2.

The SAP protein sequence was used as query sequence in homology searches in public available databases. The software programs BLAST and ClustalW were used for homology search and multi-sequence alignments, respectively. The SAP sequence was aligned to its top scoring homologs of tissue-nonspecific ALPs found in mouse (Accession number P09242), human (A. n. P05186), chicken (A. n. Q92058) and an ALP of the silk moth *Bombyx mori* (A. n. P29523). The alignment is shown in FIG. 3. No sequence equivalent of the cDNA is found by homology searches in public available databases. The derived protein sequence, however, scores relative high homology to a number of known ALPs having 44% identity and 60% similarity in amino acid sequences. Protein homologies were searched in the SWALL database (Non-redundant protein sequence database; Swissprot+Trembl+TremblNew) running the Fasta3 program with default parameters (blosum50 matrix, gap open penalty=−12 and gap extension penalty-2, and KTUP=2) using the internet server of the European Bioinformatics Institute. [W. R. Pearson and D. J. Lipman (1988), "Improved tools for biological sequence analysis", PNAS 85:2444-2448; W. R. Pearson, (1990), "Rapid and sensitive sequence comparison with FASTP and FASTA", Methods in Enzymology 183:63-98.]

Also, the cDNA-encoded protein has the motif VTDSAA-SAT (SEQ ID NO: 36), which corresponds to the ALP active site pattern defined by Prosite PSOO 123, contained in its sequence. Thus, the isolated cDNA of a mRNA-transcript from shrimp hepatopancreas represents the gene for *P. borealis* SAP.

There is one amino acid discrepancy between the sequenced protein fragment 5ReRP6:26 and the corresponding cDNA-derived sequence. This could be explained by allelic variations in the SAP gene or by an error it the protein sequence analysis.

Sequences Used in Example 1

Protein Fragments:

```
H23:18      DINFRYASAAP(V)K      [SEQ I.D. NO. 3]

H23:30      HLITDWLDDK           [SEQ I.D. NO. 4]

5ReRP6:26   VIMGGERR             [SEQ I.D. NO. 5]

5ReRP6:17   AYWNK                [SEQ I.D. NO. 6]
```

Oligonucleotides:

```
17F:   GCITAYTGGAAYAAR              [SEQ ID. NO. 7]

26R:   CKYTCICCICCCATDATIAC         [SEQ ID. NO. 8]
where D = A + G + T
I = Inosine
K = G + T
R = A + G
Y = C + T MalpF: ATTTCGTGGGAAGAATTCGACTTTGC   [SEQ I.D. NO. 9]

MalpR: GATCTGCCAGCCTCCTGAACCA       [SEQ I.D. NO. 10]

SapF:  AARGCNTAYTGGAAYAARGAT        [SEQ ID. NO. 11]

SapR:  GAAGGTAATCATCTACATCTCA       [SEQ ID. NO. 12]
```

Example 1 has been repeated and the sequence information refined. As reflected in FIGS. 4 and 5, the cDNA gene was found to contain an open reading frame encoding a 475 amino acid protein. The cDNA of FIG. 4 has a theoretical molecular mass of 53 kDa as compared to an estimate of the mass of the purified native SAP based on SDS-PAGE of 54-55 kDa. From the multi-sequence alignments, it is believed that the SAP contains 5-10 additional amino acids at its N-terminal, bringing the molecular mass close to 54 kDa. As discussed earlier, this N-terminal region is thought to comprise some or all of the heptapeptide NPITEED (SEQ ID NO: 27), see also Example 4.

Example 2

Amino Acid Composition of cDNA-derived Protein Sequence Compared to Native SAP

Freeze-dried SAP protein was dissolved in 6 M HCl and hydrolysed at 110° C. for 24 h. After evaporation of HCl the sample was resuspended in 0.2 M sodium citrate buffer, pH 2.2, and subjected to HPLC chromatography for identification and percentage molar determination of amino acids in the hydrolysed product.

Note: This system does not differentiate between aspartate and asparagine or between glutamate and glutamine. Thus, the figures for these amino acids in the native SAP protein are combined. Also, the numbers of cysteine residues are supposedly underestimated since the protein was not oxidised.

|  | % in | |
| --- | --- | --- |
|  | cDNA-derived | Native SAP |
| Alanine | 8.3 | 9.6 |
| Aspartate + Asparagine | (13.7) | 13.6 |
| Aspartate | 10.0 | — |
| Asparagine | 3.7 | — |
| Glutamate + Glutamine | (9.0) | 11.7 |
| Glutamate | 6.7 | — |
| Glutamine | 2.3 | — |
| Cysteine | 1.0 | 0.2 |
| Phenylalanine | 4.1 | 4.1 |
| Glycine | 8.4 | 8.4 |
| Histidine | 3.7 | 2.8 |
| Isoleucine | 5.2 | 5.4 |
| Lysine | 4.6 | 4.2 |
| Leucine | 7.3 | 8.0 |
| Methionine | 1.6 | 1.9 |
| Proline | 2.7 | 3.1 |
| Arginine | 5.2 | 5.2 |
| Serine | 4.6 | 4.6 |
| Threonine | 8.7 | 8.5 |
| Valine | 5.4 | 4.9 |
| Tryptophan | 1.6 | — |
| Tyrosine | 4.1 | 3.6 |

Conclusion: For the majority of amino acids the molar ratios of each amino-acid in the cDNA-derived protein sequence are close to identical to the ratios found in the purified native protein. The apparently small disagreements are discussed above.

Thus, compared to the SAP protein the isolated cDNA encodes a protein of very similar or identical amino acid composition.

This Example and analysis has been repeated for the revised cDNA sequence and the results are presented below:

Amino acid composition of cDNA-derived protein sequence compared to native SAP.

|  | % in | |
|---|---|---|
|  | cDNA-derived | Native SAP |
| Alanine | 8.8 | 9.6 |
| Aspartate + Asparagine | — | 13.6 |
| Aspartate | 10.1 | — |
| Asparagine | 3.4 | — |
| Glutamate + Glutamine | — | 11.7 |
| Glutamate | 7.1 | — |
| Glutamine | 2.3 | — |
| Cysteine | 0.8 | 0.2 |
| Phenylalanine | 4.0 | 4.1 |
| Glycine | 8.0 | 8.4 |
| Histidine | 3.3 | 2.8 |
| Isoleucine | 5.4 | 5.4 |
| Lysine | 4.6 | 4.2 |
| Leucine | 7.6 | 8.0 |
| Methionine | 2.1 | 1.9 |
| Proline | 2.7 | 3.1 |
| Arginine | 4.8 | 5.2 |
| Serine | 4.6 | 4.6 |
| Threonine | 9.0 | 8.5 |
| Valine | 5.4 | 4.9 |
| Tryptophan | 1.5 | — |
| Tyrosine | 4.0 | 3.6 |

Example 3

Recombinant Expression of SAP in *Pichia pastoris*

The cDNA encoding SAP is used to express the enzyme heterologously in a suitable micro-organism for production of recombinant enzyme by fermentation. Several expression systems are available, and eukaryotic expression systems are preferred since these may express the enzyme at reasonable levels in its native state.

Such a system is the methylotrophic yeast *Pichia pastoris* (Invitrogen) which has been reported to express recombinant proteins at levels up to 12 g/L by intracellular expression [Clare, J. J. Raiyment, F. B., Ballantine, S. P., Sreekrishna, K. and Romanos, M. A. (1991): High-level expression of tetanus toxin fragment c in *Pichia pastoris* strains containing multiple tandem integrations of the gene. Blo/Technology 9,455-460] and up to 2.6 g/L secreted into the medium. [Paifer, E., Margolles, E., Cremata, J., Montesino. R., Herrera, L. and Delgado, J M. (1994): Efficient expression and secretion of recombinant alpha amylase in *Pichia pastoris* using two different signal sequences. Yeast 10. 1416-1419].

The inserted gene is regulated by the AOX1 (alcohol oxidase) promoter so expression may be induced by methanol.

The SAP cDNA is inserted into the commercially available vector pPIC9K. Recombinant SAP may then be expressed as a secreted product by fusion to the signal peptide sequence derived from *S. cerevisiae* α-factor contained in the vector. When integrated into a his − strain (KM71 or GS115) strains are selected for recombinants by selection of his + clones in a histidine-free medium, since the his genotype is complemented by the vector insert. Furthermore, recombinants are screened for multiple gene inserts by resistance to increased-concentrations of Geneticin (G418, Invitrogen) acquired by the plasmid-borne kanamycin-resistance gene.

In detail, the PCR-generated SAP cDNA is used as a template in a new PCR reaction in order to generate a new PCR product containing proper restriction sites for integration into the pPIC9K vector in frame with the α-factor signal sequence. As the forward primer for the PCR reaction, a modified "17F" primer [SEQ. ID. No. 13] is used, replacing ATG codon (Met) with a lysine codon (AAG) in order to reconstruct a putative lysine residue cleaved off by trypsin. The reverse primer [SEQ. ID. No. 14] is constructed in order to attach a NotI restriction site 3' to the stop codon of the SAP cDNA sequence.

The resulting PCR product is cut with NotI and ligated into a pPIC9K vector previously cut with SnaBI and NotI (resulting in plasmid pPIC9K-SAP). Since the vector is blunt-ended by SnaBI at the 5' joining site, and both termini are in reading frame, no further modification of the 5'-terminus of the modified cDNA is necessary.

The vector is then propagated by transformation of a competent *E. coli* strain like TOP10F' (Invitrogen) or equivalent, and recombinants are selected by their resistance to ampicillin. Isolated pP109K-SAP plasmid may then be linearized by restriction cutting with SocI in order to create a vector cassette to be inserted into The AOXI gene of *Pichia pastoris*. After transformation of *Pichia pastoris* cells (strains GS115 or KM71) with linearized pPIC9K-SAP construct, recombinants are selected from his + mutants according to the manufacturer's protocol.

Isolated colonies are tested for expression of recombinant SAP into the medium by growing cells in the presence of methanol according to the method recommended by the manufacturer. If desired, further increases in expression levels are achieved by screening recombinant strains for clones containing multiple copies of the recombinant gene. This is done by cultivating his + mutants in the presence of increasing levels of the antibiotic G418 (Invitrogen). Clones growing at high G418 levels are likely to contain multiple copies of the gene.

All methods of cultivation, transformation and selection are described in detail in protocols available from the supplier of the *Pichia pastoris* system (Invitrogen, The Netherlands).

The modified SAP construct yields a recombinant product where 5 amino acids (EAEAY) (SEQ ID NO: 37) are added from the remaining signal recognition sequence of the signal peptidase KEX2 of *Pichia pastoris*. This N-terminal sequence results in a final product that is slightly truncated, but in reasonable consensus with other alkaline phosphatases, still containing a recognition sequence for Pichia pastoris signal peptidase.

Primers Used in Example 3

```
Forward:
AAGGCITAYTGGAAYAAR        [SEQ. ID. No. 13]
where
I = Inosine
R = A + G
Y = C + T Reverse:
TACAGCGGCCGCCATCTOAI11TTCG    [SEQ. ID. No. 14]
```

Example 4

Expression of SAP in *Escherichia coli* TOP10

Determination of the SAP-signal Sequence

The N-terminal signal sequence of SAP was determined by 5'-RACE using cDNA as a template. mRNA was isolated from 100 mg of shrimp (*Pandalus Borealis*) hepatopancreas using the Oligotex Direct mRNA Mini Kit (Qiagen) as described by manufacturer. Shrimp hepatopancreas cDNA was made using SMART PCR cDNA synthesis Kit (Clontech) following the protocol described by the manufacturer. The cDNA was blunt ended and purified by adding 40 Ag proteinase K to 50 Al of the cDNA and incubated at 45° C. for 45 min and 90° C. for 8 min, and then adding 15 U T4-DNA polymerase (Promega) and incubated at 16° C. for 30 min and at 72° C. for 10 min. Finally the cDNA was extracted two times in phenol/chlorophorm and ethanol precipitated. RACE-adaptors were ligated to the cDNA as described in Marathon cDNA amplification kit (Clontech). The 5'-RACE reaction was done in a final volume of 50 Al using the Advantage cDNA polymerase mix (Clontech) and a APl-primer (supplied with the Marathon cDNA amplification kit) and a SAP-specific primer (5'-GCG TGG TGC ATA TGG ICA ATC CGT CC-3') (SEQ ID NO: 23) and 5 Al 50 times diluted adaptor ligated eDNA as template. The RACE PCR-reaction was done in a Biometra TGradient thermocycler with a initial denaturation step of 94° C. for 30 seconds, followed by 5 cycles of 94° C. for 5 sec and 72° C. for 3 mm, 5 cycles of 94 C. for 5 sec and 70° C. for 3 mm and 30 cycles of 94° C. for 5 sec and 68° C. for 3 min. The 1200 bp SAP-fragment generated was purified from the agarose gel, re-amplified using PCR and sequenced.

Cloning of SAP into pBAD/gIII A Expression Vector

To clone the SAP-gene into the pBAD/gIII A vector, the SAP-gene was PCR-amplified with two primers containing a Sad and Hindlil site, respectively (underlined). Based on the full length SAP-sequence obtained (signal sequence in addition to the main sequence), the primers were designed to amplify the SAP-gene with the amino acids NPITEEDKAY-WNK . . . (SEQ ID NO: 38) as N-terminus. In addition, three bases were changed in primer 1 (from C to A, A to C, and A to C) in order to codon-optimize three of the N-terminal codons (denoted with small letters in the primer sequence) (Primer 1 : 5'-ATG GAG CTC AAC CCa ATc ACc GAA GAA GAC AA-3' (SEQ ID NO: 24) Primer 2: 5'-ATG AAG CTT TCA TTT TTC GTC ACA GAA AGT G-3' (SEQ ID NO: 39)). The PCR was carried out in a final volume of 50 Al containing 10 AM of each of the two primers, 1.5 U Pfu-polymerase (Promega) and buffer supplied, 0.2 mM dNTP and 10 ng shrimp hepatopancreas cDNA as a template. PCR was done with a initial denaturation step of 94° C. for 30 sec followed by 30 cycles of 94° C. for 15 sec, 55° C. for 1 min and 72° C. for 3 min. The PCR-product was purified with Qiaquick PCR purification kit (Qiagen).

Both the pBAD/gIII A vector and the SAP PCR-product was treated with 5U of SacI and HindIII restriction enzymes, respectively. The SAP PCR-product was ligated into the vector in a 10 µl reaction using 1 U T4-DNA ligase (USB) and approximately 1 mg of both plasmid and PCR-product. The reaction mix was incubated at 16° C. for 16 h. The ligation mix was then used to transform $E.\ coli$ TOP10 cells by adding the ligation mix to 40 µl electrocompetent $E.\ coli$ TOP10 cells and electroporated at 1800 V. Immediately after electroporation, 1 ml SOC-medium was added and incubated at 37° C. for 1 h. The cells were then plated on LB-plates containing 100 mg/ml ampicillin for selection of transformed cells.

Expression of SAP in $E.\ coli$ TOP10

Two $E.\ coli$ TOP10 colonies containing the recombinant pBAD/gIII A vector containing the SAP-gene were selected for expression. An $E.\ coli$ TOP10 strain containing a empty pBAD/gIII vector was used as negative control.

Three Erlenmeyer flasks containing 50 ml LB-medium were inoculated with 2.5 ml overnight cultures in LB-medium supplied with 100 µg/ml ampicillin. The cells were grown at 30° C. with shaking until the cells reached a density of $OD_{600}$ ≈0.5. Each of the three cultures were then splitted into two (2×25 ml), where one of the two cultures were induced by adding L-arabinose to a final concentration of 0.05% (w/v). All cell-cultures were further grown at 30° C. with shaking for 3 h before the cells were harvested.

Analysing the Expression Cultures

From each of the expression cultures, a 200 µl sample were centrifuged and the supernatants were removed. To the cell pellets, 100 µl 1× SDS-PAGE sample buffer was added and incubated at 100° C. for 3 min and centrifuged 18.000 g for 3 min. The cell lysates were then directly applied and analysed on a SDS-PAGE gel. An additional SDS-PAGE gel was further electroblotted to transfer the proteins to a nitrocellulose blotting membrane (0.45 um, Bio-Rad) and immunostained using a antibody raised against SAP purified from the shrimp processing water and Goat Anti-Rabbit IgG (H+L) (Human IgG Adsorbed) Horseradish Peroxidase Conjugate (Bio-Rad). Standard protocols for SDS-PAGE, electroblotting and immunostaining were followed.

Figure 11:
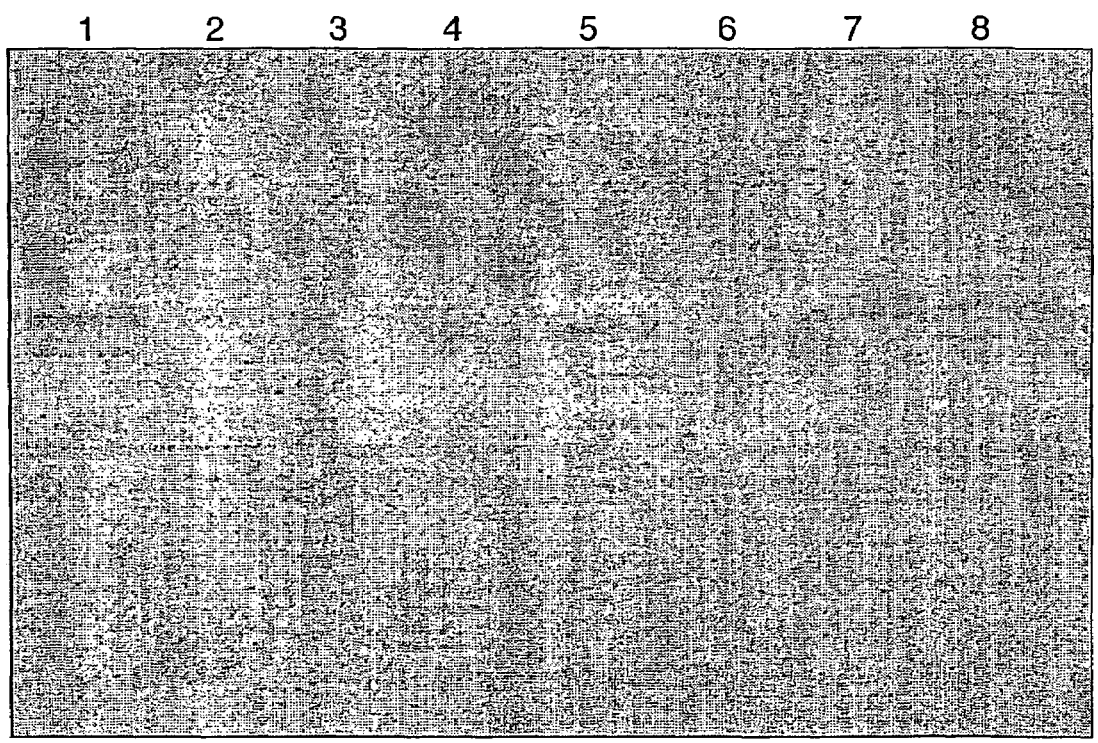
FIG. 11 is a photo of an immunoblot of total cell protein extracts from the expression cultures of Example 4, in which Lane: 1 and 8: SAP 50 ng, Lane 2: negative control culture, non induced, Lane 3: negative control culture, induced, Lane 4: SAP-culture 1, non-induced, Lane 5: SAP-culture 1, induced, Lane 6: SAP-culture 2, non-induced, Lane 7: SAP-culture 2, induced.

As shown in FIGS. 10 and 11, recombinant SAP is expressed using the pBAD/gIII A vector and $E.\ coli$ TOP10 cells as a host. Both recombinant $E.\ coli$ strains containing recombinant pBAD/gIII A-SAP vectors produce recombinant SAP, whereas the negative control did not give any signal on the western blot (FIG. 11).

The invention claimed is:

1. An isolated nucleic acid molecule comprising a nucleotide sequence as set forth in any one of SEQ ID Nos. 1, 15, or 20 or having at least 95% sequence identity therewith, which encodes a heat labile alkaline phosphatase, or the complementary sequence of said sequences.

2. An isolated nucleic acid molecule comprising a nucleotide sequence which encodes a heat labile alkaline phosphatase, said alkaline phosphatase comprising the amino acid sequence of SEQ ID No. 2 or SEQ ID No. 16, or variants of said amino acid sequences which are at least 95% identical thereto or the complementary sequence of said nucleotide sequence.

3. The nucleic acid molecule of claim 1 wherein the alkaline phosphatase is *Pandalus borealis* alkaline phosphatase.

4. A genetic construct comprising a nucleic acid molecule of claim 1 operably linked to a promoter sequence.

5. A recombinant expression vector comprising a nucleic acid molecule of claim 1 and which is capable of propagation in a host cell.

6. The vector of claim 5 which is a plasmid or viral vector.

7. An isolated cell transformed with a construct or vector of claim 4 or 5.

8. The cell of claim 7 which is a prokaryotic cell.

9. The cell of claim 7 which is part of a eukaryotic cell culture.

10. An isolated recombinant cell or microorganism comprising a nucleic acid molecule of claim 1.

11. An isolated recombinant cell transformed with a nucleic acid molecule which encodes a heat labile alkaline phosphatase which comprises the amino acid sequence of SEQ ID No. 2 or SEQ ID No. 16 or an amino acid sequence which has at least 95% sequence identity with SEQ ID No. 2 or SEQ ID No. 16.

12. A method for the manufacture of heat labile alkaline phosphatase, comprising transforming a host cell with the vector of claim 9, maintaining the cell in a culture medium and isolating heat labile alkaline phosphatase expressed by said cell.

13. The nucleic acid molecule of claim 1, wherein said nucleic acid molecule comprises the nuecleotide sequence as set forth in SEQ ID No. 15.

14. The nucleic acid molecule of claim 2, wherein said alkaline phosphatase comprises the amino acid sequence as set forth in SEQ ID No. 16.

15. The nucleic acid molecule of claim 1, wherein said nucleic acid molecule comprises the nucleotide sequence as set forth in SEQ ID No. 1.

16. The nucleic acid molecule of claim 1, wherein said nucleic acid molecule comprises the nucleotide sequence as set forth in SEQ ID No. 20.

17. The nucleic acid molecule of claim 2, wherein said alkaline phosphatase comprises the amino acid sequence as set forth in SEQ ID No. 2.

* * * * *

SEQUENCE LISTING

<160> NUMBER OF SEQ ID NOS: 25

<210> SEQ ID NO 1
<211> LENGTH: 1481
<212> TYPE: DNA
<213> ORGANISM: Pandalus borealis

<400> SEQUENCE: 1
gatgcccaag atgcactgga taaacagctg gggataaaac tgcgagagaa gcaggccaag    60
aacgtgatct tcttcctagg agacgggatg tccctcagta cagttaccgc agcaagaatc   120
tacaaaggtg gattgaccgg gaaatttgaa cgggaaaaga tttcgtggga agaattcgac   180

```
tttgctgctt tgagtaagac gtacaatacg acaagcaag tgacagatag tgctgccagt    240
gccacagcct acctcactgg ggtgaagacc aaccaggag tcatcggcct tgatgccaat     300
accgtgagaa caaactgctc ttaccaactt gatgaatccc tcttcactta ctccatcgcc   360
cattggttcc aggaggctgg cagatcaaca ggtgtcgtga catcgaccag ggtaactcat   420
gctactcctg caggaactta tgctcacgtg gctgacagag attgggagaa cgacagtgat   480
gttgtccacg acagagaaga tccagaaata tgtgatgaca tagctgaaca actggtattc   540
agagaacctg gaaagaactt caaggtcatc atgggcggcg tcggcgtgg attctttcct    600 gaggaagcgc ttgatatcga agatggcatt ccagggaaa gggaagatgg caaacacctc    660
ataaccgatt ggttggacga taaggcatct cagggagcca cagcatcgta tgtctggaac   720
cgagatgatc tattggctgt tgacattcga aacacagact accttatggg actgttttca   780
tacacacatc tagacacagt tttaaccaga acgccgaaa tggatcccac cttgccggaa    840
atgacaaagg tcgccatcga aatgctgacg aaggatgaaa atggcttttt cctcttagta   900
gaaggtggac ggattgacca tatgcaccac gccaatcaga tccgtcagtc gttagcggag   960
acgctggaca tggaggaaag ctgtatccat ggctctctct atgacagacc cagaggaaac  1020
aatcatttct gggtcacagc tgatcacggt cacactctca ccatcactgg atacgcagac  1080
aggaacaccg atattttgga tttcgccggc atcagcgact ggatgatag gaggtacacc   1140 atcctggact atggcagtgg acctggatat catatcacgg aagatggcaa acgttacgaa   1200
cctacagagg aagatttgaa agacatcaat ttccgctacg catcggcagc gcccaagcat  1260
tcagttaccc atgatggcac agacgttggt atttgggtca acggaccttt cgctcatctc   1320
ttcacggtca cgggtgtcta tgaagagaat tacattcccc acgccttggc ctacgcagcc   1380
tgcgttggta caggacgcac tttctgtgac gaaaaatgag atgtagatga ttaccttctt  1440
aagtacatta aagattgcaa aaaaaaaaa aaaaaaaaa a                         1481
```

<210> SEQ ID NO 2
<211> LENGTH: 478
<212> TYPE: PRT
<213> ORGANISM: Pandalus borealis
<220> FEATURE:
<221> NAME/KEY: ACT_SITE
<222> LOCATION: (80)..(88)

<400> SEQUENCE: 2

```
Lys Ala Tyr Trp Asn Lys Asp Ala Gln Asp Ala Leu Asp Lys Gln Leu
1               5                   10                  15

Gly Ile Lys Leu Arg Glu Lys Gln Ala Lys Asn Val Ile Phe Phe Leu
            20                  25                  30

Gly Asp Gly Met Ser Leu Ser Thr Val Thr Ala Ala Arg Ile Tyr Lys
        35                  40                  45

Gly Gly Leu Thr Gly Lys Phe Glu Arg Glu Lys Ile Ser Trp Glu Glu
    50                  55                  60

Phe Asp Phe Ala Ala Leu Ser Lys Thr Tyr Asn Thr Asp Lys Gln Val
65                  70                  75                  80

Thr Asp Ser Ala Ala Ser Ala Thr Ala Tyr Leu Thr Gly Val Lys Thr
                85                  90                  95

Asn Gln Gly Val Ile Gly Leu Asp Ala Asn Thr Val Arg Thr Asn Cys
            100                 105                 110

Ser Tyr Gln Leu Asp Glu Ser Leu Phe Thr Tyr Ser Ile Ala His Trp
        115                 120                 125
```

-continued

```
Phe Gln Glu Ala Gly Arg Ser Thr Gly Val Val Thr Ser Thr Arg Val
    130                 135                 140

Thr His Ala Thr Pro Ala Gly Thr Tyr Ala His Val Ala Asp Arg Asp
145                 150                 155                 160

Trp Glu Asn Asp Ser Asp Val Val His Asp Arg Glu Asp Pro Glu Ile
                165                 170                 175

Cys Asp Asp Ile Ala Glu Gln Leu Val Phe Arg Glu Pro Gly Lys Asn
            180                 185                 190

Phe Lys Val Ile Met Gly Gly Arg Arg Gly Phe Phe Pro Glu Glu
        195                 200                 205

Ala Leu Asp Ile Glu Asp Gly Ile Pro Gly Glu Arg Glu Asp Gly Lys
    210                 215                 220

His Leu Ile Thr Asp Trp Leu Asp Asp Lys Ala Ser Gln Gly Ala Thr
225                 230                 235                 240

Ala Ser Tyr Val Trp Asn Arg Asp Asp Leu Leu Ala Val Asp Ile Arg
                245                 250                 255

Asn Thr Asp Tyr Leu Met Gly Leu Phe Ser Tyr Thr His Leu Asp Thr
            260                 265                 270

Val Leu Thr Arg Asp Ala Glu Met Asp Pro Thr Leu Pro Glu Met Thr
        275                 280                 285

Lys Val Ala Ile Glu Met Leu Thr Lys Asp Glu Asn Gly Phe Phe Leu
    290                 295                 300

Leu Val Glu Gly Gly Arg Ile Asp His Met His His Ala Asn Gln Ile
305                 310                 315                 320

Arg Gln Ser Leu Ala Glu Thr Leu Asp Met Glu Glu Ser Cys Ile His
                325                 330                 335

Gly Ser Leu Tyr Asp Arg Pro Arg Gly Asn Asn His Phe Trp Val Thr
            340                 345                 350

Ala Asp His Gly His Thr Leu Thr Ile Thr Gly Tyr Ala Asp Arg Asn
        355                 360                 365

Thr Asp Ile Leu Asp Phe Ala Gly Ile Ser Asp Leu Asp Asp Arg Arg
    370                 375                 380

Tyr Thr Ile Leu Asp Tyr Gly Ser Gly Pro Gly Tyr His Ile Thr Glu
385                 390                 395                 400

Asp Gly Lys Arg Tyr Glu Pro Thr Glu Glu Asp Leu Lys Asp Ile Asn
                405                 410                 415

Phe Arg Tyr Ala Ser Ala Ala Pro Lys His Ser Val Thr His Asp Gly
            420                 425                 430

Thr Asp Val Gly Ile Trp Val Asn Gly Pro Phe Ala His Leu Phe Thr
        435                 440                 445

Val Thr Gly Val Tyr Glu Glu Asn Tyr Ile Pro His Ala Leu Ala Tyr
    450                 455                 460

Ala Ala Cys Val Gly Thr Gly Arg Thr Phe Cys Asp Glu Lys
465                 470                 475
```

```
<210> SEQ ID NO 3
<211> LENGTH: 13
<212> TYPE: PRT
<213> ORGANISM: Pandalus borealis
<220> FEATURE:
<221> NAME/KEY: misc_feature
<222> LOCATION: ()..()
<223> OTHER INFORMATION: Trypsin digestion product of Shrimp Alkaline
      Phosphatase

<400> SEQUENCE: 3
```

Asp Ile Asn Phe Arg Tyr Ala Ser Ala Ala Pro Val Lys
1               5                   10

<210> SEQ ID NO 4
<211> LENGTH: 10
<212> TYPE: PRT
<213> ORGANISM: Pandalus borealis
<220> FEATURE:
<221> NAME/KEY: misc_feature
<222> LOCATION: ()..()
<223> OTHER INFORMATION: Trypsin digestion product of Shrimp Alkaline
      Phosphatase

<400> SEQUENCE: 4

His Leu Ile Thr Asp Trp Leu Asp Asp Lys
1               5                   10

<210> SEQ ID NO 5
<211> LENGTH: 8
<212> TYPE: PRT
<213> ORGANISM: Pandalus borealis
<220> FEATURE:
<221> NAME/KEY: misc_feature
<222> LOCATION: ()..()
<223> OTHER INFORMATION: Trypsin digestion product of Shrimp Alkaline
      Phosphatase

<400> SEQUENCE: 5

Val Ile Met Gly Gly Glu Arg Arg
1               5

<210> SEQ ID NO 6
<211> LENGTH: 5
<212> TYPE: PRT
<213> ORGANISM: Pandalus borealis
<220> FEATURE:
<221> NAME/KEY: misc_feature
<222> LOCATION: ()..()
<223> OTHER INFORMATION: Trypsin digestion product of Shrimp Alkaline
      Phosphatase

<400> SEQUENCE: 6

Ala Tyr Trp Asn Lys
1               5

<210> SEQ ID NO 7
<211> LENGTH: 15
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (3)...(3)
<223> OTHER INFORMATION: I

<400> SEQUENCE: 7
gcntaytgga ayaar                                                      15

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (6)...(6)
<223> OTHER INFORMATION: I

```
<220> FEATURE:
<221> NAME/KEY: modified_base
<222> LOCATION: (9)...(9)
<223> OTHER INFORMATION: I
<220> FEATURE:
<221> NAME/KEY: modified_base
<222> LOCATION: (18)...(18)
<223> OTHER INFORMATION: I

<400> SEQUENCE: 8
ckytcnccnc ccatdatnac                                              20

<210> SEQ ID NO 9
<211> LENGTH: 26
<212> TYPE: DNA
<213> ORGANISM: Artificial Sequence
<220> FEATURE:
<223> OTHER INFORMATION: Oligonucleotide

<400> SEQUENCE: 9
atttcgtggg aagaattcga ctttgc                                       26

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide

<400> SEQUENCE: 10
gatctgccag cctcctggaa cca                                          23

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (6)..(6)
<223> OTHER INFORMATION: n = t, a, g or c

<400> SEQUENCE: 11
aargcntayt ggaayaarga t                                            21

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide

<400> SEQUENCE: 12
gaaggtaatc atctacatct ca                                           22

<210> SEQ ID NO 13
<211> LENGTH: 18
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (6)..(6)
<223> OTHER INFORMATION: I

<400> SEQUENCE: 13
```

|  |  |
|---|---|
| aaggcntayt ggaayaar | 18 |

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14

|  |  |
|---|---|
| tacagcggcc gccatctcat ttttcg | 26 |

<210> SEQ ID NO 15
<211> LENGTH: 1490
<212> TYPE: DNA
<213> ORGANISM: Pandalus borealis
<220> FEATURE:
<221> NAME/KEY: modified_base
<222> LOCATION: (6)..(6)
<223> OTHER INFORMATION: n = t, a, g or c

<400> SEQUENCE: 15

|  |  |
|---|---|
| aargcntayt ggaayaarga tgcccaagat gcactggata acagctggg gataaaactg | 60 |
| cgagagaagc aggccaagaa cgtgatcttc ttcctaggag acgggatgtc cctcagtaca | 120 |
| gttaccgcag caagaatcta caaaggtgga ttgaccggga aatttgaacg ggaaaagatt | 180 |
| tcgtgggaag aattcgactt tgctgctttg agtaagacgt acaatacgga caagcaagtg | 240 |
| acagatagtg ctgccagtgc cacagcctac ctcactgggg tgaagaccaa ccagggagtc | 300 |
| atcggccttg atgccaatac cgtgagaaca aactgctctt accaacttga tgaatccctc | 360 |
| ttcacttact ccatcgccca ttggttccag gaggctggca gatcaacagg tgtcgtgaca | 420 |
| tcgaccaggg taactcatgc tactcctgca ggaacttatg ctcacgtggc tgacagagat | 480 |
| tgggagaacg acagtgatgt tgtccacgac agagaagatc cagaaatatg tgatgacata | 540 |
| gctgaacaac tggtattcag agaacctgga agaacttca aggtcatcat gggcggcggt | 600 |
| cggcgtggat tctttcctga ggaagcgctt gatatcgaag atggcattcc agggaaagg | 660 |
| gaagatggca acacctcat aaccgattgg ttggacgata aggcatctca gggagccaca | 720 |
| gcatcgtatg tctggaaccg agatgatcta ttggctgttg acattcgaaa cacagactac | 780 |
| cttatgggac tgttttcata cacacatcta gacacagttt taaccagaga cgccgaaatg | 840 |
| gatcccacct tgccggaaat gacaaaggtc gccatcgaaa tgctgacgaa ggatgaaaat | 900 |
| ggcttttttcc tcttagtaga aggtggacgg attgaccata tgcaccacgc caatcagatc | 960 |
| cgtcagtcgt tagcggagac gctggacatg gaggaagctg tatccatggc tctctctatg | 1020 |
| acagacccag aggaaacaat cattctggtc acagctgatc acggtcacac tctcaccatc | 1080 |
| actggatacg cagacaggaa caccgatatt ttggatttcg ccggcatcag cgacttggat | 1140 |
| gataggaggt acaccatcct ggactatggc agtggacctg gatatcatat cacgaagat | 1200 |
| ggcaaacgtt acgaacctac agaggaagat ttgaaagaca tcaatttccg ctacgcatcg | 1260 |
| gcagcgccca gcattcagt tacccatgat ggcacagacg ttggtatttg ggtcaacgga | 1320 |
| cctttcgctc atctcttcac gggtgtctat gaagagaatt acattcccca cgccttggcc | 1380 |
| tacgcagcct gcgttggtac aggacgcact ttctgtgacg aaaaatgaga tgtagatgat | 1440 |
| taccttctta agtacattaa agattgcaaa aaaaaaaaa aaaaaaaaa | 1490 |

<210> SEQ ID NO 16
<211> LENGTH: 475

```
<212> TYPE: PRT
<213> ORGANISM: Pandalus borealis
<220> FEATURE:
<221> NAME/KEY: ACT_SITE
<222> LOCATION: (80)..(88)

<400> SEQUENCE: 16
```

| | | | | | | | | | | | | | | |
|---|---|---|---|---|---|---|---|---|---|---|---|---|---|---|
| Lys | Ala | Tyr | Trp | Asn | Lys | Asp | Ala | Gln | Asp | Ala | Leu | Asp | Lys | Gln | Leu |
| 1 | | | | 5 | | | | | 10 | | | | | 15 | |

Gly Ile Lys Leu Arg Glu Lys Gln Ala Lys Asn Val Ile Phe Phe Leu
                20                  25                  30

Gly Asp Gly Met Ser Leu Ser Thr Val Thr Ala Ala Arg Ile Tyr Lys
            35                  40                  45

Gly Gly Leu Thr Gly Lys Phe Glu Arg Glu Lys Ile Ser Trp Glu Glu
    50                  55                  60

Phe Asp Phe Ala Ala Leu Ser Lys Thr Tyr Asn Thr Asp Lys Gln Val
65                  70                  75                  80

Thr Asp Ser Ala Ala Ser Ala Thr Ala Tyr Leu Thr Gly Val Lys Thr
                85                  90                  95

Asn Gln Gly Val Ile Gly Leu Asp Ala Asn Thr Val Arg Thr Asn Cys
            100                 105                 110

Ser Tyr Gln Leu Asp Glu Ser Leu Phe Thr Tyr Ser Ile Ala His Trp
        115                 120                 125

Phe Gln Glu Ala Gly Arg Ser Thr Gly Val Val Thr Ser Thr Arg Val
    130                 135                 140

Thr His Ala Thr Pro Ala Gly Thr Tyr Ala His Val Ala Asp Arg Asp
145                 150                 155                 160

Trp Glu Asn Asp Ser Asp Val Val His Asp Arg Glu Asp Pro Glu Ile
                165                 170                 175

Cys Asp Asp Ile Ala Glu Gln Leu Val Phe Arg Glu Pro Gly Lys Asn
            180                 185                 190

Phe Lys Val Ile Met Gly Gly Arg Arg Gly Phe Phe Pro Glu Glu
        195                 200                 205

Ala Leu Asp Ile Glu Asp Gly Ile Pro Gly Glu Arg Glu Asp Gly Lys
    210                 215                 220

His Leu Ile Thr Asp Trp Leu Asp Lys Ala Ser Gln Gly Ala Thr
225                 230                 235                 240

Ala Ser Tyr Val Trp Asn Arg Asp Asp Leu Leu Ala Val Asp Ile Arg
                245                 250                 255

Asn Thr Asp Tyr Leu Met Gly Leu Phe Ser Tyr Thr His Leu Asp Thr
            260                 265                 270

Val Leu Thr Arg Asp Ala Glu Met Asp Pro Thr Leu Pro Glu Met Thr
        275                 280                 285

Lys Val Ala Ile Glu Met Leu Thr Lys Asp Glu Asn Gly Phe Phe Leu
    290                 295                 300

Leu Val Glu Gly Gly Arg Ile Asp His Met His Ala Asn Gln Ile
305                 310                 315                 320

Arg Gln Ser Leu Ala Glu Thr Leu Asp Met Glu Glu Ala Val Ser Met
                325                 330                 335

Ala Leu Ser Met Thr Asp Pro Glu Thr Ile Ile Leu Val Thr Ala
            340                 345                 350

Asp His Gly His Thr Leu Thr Ile Thr Gly Tyr Ala Asp Arg Asn Thr
        355                 360                 365

Asp Ile Leu Asp Phe Ala Gly Ile Ser Asp Leu Asp Asp Arg Arg Tyr
    370                 375                 380

```
Thr Ile Leu Asp Tyr Gly Ser Gly Pro Gly Tyr His Ile Thr Glu Asp
385                 390                 395                 400

Gly Lys Arg Tyr Glu Pro Thr Glu Glu Asp Leu Lys Asp Ile Asn Phe
                405                 410                 415

Arg Tyr Ala Ser Ala Ala Pro Lys His Ser Val Thr His Asp Gly Thr
                420                 425                 430

Asp Val Gly Ile Trp Val Asn Gly Pro Phe Ala His Leu Phe Thr Gly
                435                 440                 445

Val Tyr Glu Glu Asn Tyr Ile Pro His Ala Leu Ala Tyr Ala Ala Cys
        450                 455                 460

Val Gly Thr Gly Arg Thr Phe Cys Asp Glu Lys
465                 470                 475
```

<210> SEQ ID NO 17
<211> LENGTH: 141
<212> TYPE: DNA
<213> ORGANISM: Pandalus borealis

<400> SEQUENCE: 17

```
atgagggctt tctactgtct atttgggtta cttttaaccc taagtcttca aggagaagca    60
acacgtcaac aagttccta tgatggagat gagtaccacg agagatatcc gggtcaatcc   120
aaccccataa cagaagaaga c                                             141
```

<210> SEQ ID NO 18
<211> LENGTH: 47
<212> TYPE: PRT
<213> ORGANISM: Pandalus borealis
<220> FEATURE:
<221> NAME/KEY: SIGNAL
<222> LOCATION: (41)..(47)

<400> SEQUENCE: 18

```
Met Arg Ala Phe Tyr Cys Leu Phe Gly Leu Leu Thr Leu Ser Leu
1               5                   10                  15

Gln Gly Glu Ala Thr Arg Gln Pro Ser Ser Tyr Asp Gly Asp Glu Tyr
                20                  25                  30

His Glu Arg Tyr Pro Gly Gln Ser Asn Pro Ile Thr Glu Glu Asp
            35                  40                  45
```

<210> SEQ ID NO 19
<211> LENGTH: 18
<212> TYPE: DNA
<213> ORGANISM: Artificial Sequence
<220> FEATURE:
<223> OTHER INFORMATION: Corresponds to the dengenerate coding sequence
      for the peptide sequence KAYWNK
<220> FEATURE:
<221> NAME/KEY: modified_base
<222> LOCATION: (6)..(6)
<223> OTHER INFORMATION: n = t, a, g or c

<400> SEQUENCE: 19

```
aargcntayt ggaayaar                                                  18
```

<210> SEQ ID NO 20
<211> LENGTH: 1499
<212> TYPE: DNA
<213> ORGANISM: Artificial Sequence
<220> FEATURE:
<223> OTHER INFORMATION: Combination of SEQ ID Nos 19 and 1
<220> FEATURE:
<221> NAME/KEY: modified_base

```
<222> LOCATION: (6)..(6)
<223> OTHER INFORMATION: n = t, a, g or c

<400> SEQUENCE: 20
aargcntayt ggaayaarga tgcccaagat gcactggata acagctggg gataaaactg      60 cgagagaagc aggccaagaa cgtgatcttc ttcctaggag acgggatgtc cctcagtaca     120
gttaccgcag caagaatcta caaaggtgga ttgaccggga aatttgaacg ggaaaagatt     180
tcgtgggaag aattcgactt tgctgctttg agtaagacgt acaatacgga caagcaagtg     240
acagatagtg ctgccagtgc cacagcctac ctcactgggg tgaagaccaa ccagggagtc     300
atcggccttg atgccaatac cgtgagaaca aactgctctt accaacttga tgaatccctc     360
ttcacttact ccatcgccca ttggttccag gaggctggca gatcaacagg tgtcgtgaca     420
tcgaccaggg taactcatgc tactcctgca ggaacttatg ctcacgtggc tgacagagat     480
tgggagaacg acagtgatgt tgtccacgac agagaagatc cagaaatatg tgatgacata     540
gctgaacaac tggtattcag agaacctgga agaacttca aggtcatcat gggcggcggt      600
cggcgtggat tctttcctga ggaagcgctt gatatcgaag atggcattcc aggggaaagg     660
gaagatggca acacctcat aaccgattgg ttggacgata aggcatctca gggagccaca      720
gcatcgtatg tctggaaccg agatgatcta ttggctgttg acattcgaaa cacagactac     780
cttatgggac tgttttcata cacacatcta gacacagttt taaccagaga cgccgaaatg     840
gatcccacct gccggaaat gacaaaggtc gccatcgaaa tgctgacgaa ggatgaaaat      900 ggcttttcc tcttagtaga aggtggacgg attgaccata tgcaccacgc caatcagatc      960
cgtcagtcgt tagcggagac gctggacatg gaggaaagct gtatccatgg ctctctctat    1020
gacagaccca gaggaaacaa tcatttctgg gtcacagctg atcacggtca cactctcacc    1080
atcactggat acgcagacag gaacaccgat attttggatt tcgccggcat cagcgacttg    1140
gatgatagga ggtacaccat cctggactat ggcagtggac ctggatatca tatcacggaa    1200
gatggcaaac gttacgaacc tacagaggaa gatttgaaag acatcaattt ccgctacgca    1260
tcggcagcgc ccaagcattc agttacccat gatggcacag acgttggtat ttgggtcaac    1320
ggacctttcg ctcatctctt cacggtcacg ggtgtctatg aagagaatta cattccccac    1380
gccttggcct acgcagcctg cgttggtaca ggacgcactt tctgtgacga aaatgagat     1440 gtagatgatt accttcttaa gtacattaaa gattgcaaaa aaaaaaaaa aaaaaaaa       1499

<210> SEQ ID NO 21
<211> LENGTH: 18
<212> TYPE: DNA
<213> ORGANISM: Pandalus borealis

<400> SEQUENCE: 21
aaagcatatt ggaacaaa                                                      18

<210> SEQ ID NO 22
<211> LENGTH: 1511
<212> TYPE: DNA
<213> ORGANISM: Artificial Sequence
<220> FEATURE:
<223> OTHER INFORMATION: Combination of SEQ ID No 15 (whose first 18
      bases, corresponding to SEQ ID No 19, have been replaced by SEQ ID
      No 21) and the last 21 bases of SEQ ID No 17

<400> SEQUENCE: 22
aaccccataa cagaagaaga caaagcatat tggaacaaag atgcccaaga tgcactggat      60
```

-continued

```
aaacagctgg ggataaaact gcgagagaag caggccaaga acgtgatctt cttcctagga      120
gacgggatgt ccctcagtac agttaccgca gcaagaatct acaaaggtgg attgaccggg      180
aaatttgaac gggaaaagat ttcgtgggaa gaattcgact ttgctgcttt gagtaagacg      240
tacaatacgg acaagcaagt gacagatagt gctgccagtg ccacagccta cctcactggg      300
gtgaagacca accagggagt catcggcctt gatgccaata ccgtgagaac aaactgctct      360
taccaacttg atgaatccct cttcacttac tccatcgccc attggttcca ggaggctggc      420
agatcaacag gtgtcgtgac atcgaccagg gtaactcatg ctactcctgc aggaacttat      480
gctcacgtgg ctgacagaga ttgggagaac gacagtgatg ttgtccacga cagagaagat      540
ccagaaatat gtgatgacat agctgaacaa ctggtattca gagaacctgg aaagaacttc      600
aaggtcatca tgggcggcgg tcggcgtgga ttctttcctg aggaagcgct tgatatcgaa      660
gatggcattc caggggaaag ggaagatggc aaacacctca taccgattg gttggacgat       720 aaggcatctc agggagccac agcatcgtat gtctggaacc gagatgatct attggctgtt      780
gacattcgaa acacagacta ccttatggga ctgttttcat acacacatct agacacagtt      840
ttaaccagag acgccgaaat ggatcccacc ttgccggaaa tgacaaaggt cgccatcgaa      900
atgctgacga aggatgaaaa tggcttttt ctcttagtag aaggtggacg gattgaccat       960
atgcaccacg ccaatcagat ccgtcagtcg ttagcggaga cgctggacat ggaggaagct     1020
gtatccatgg ctctctctat gacagaccca gaggaaacaa tcattctggt cacagctgat     1080
cacggtcaca ctctccaccat cactggatac gcagacagga acaccgatat tttggatttc      1140
gccggcatca gcgacttgga tgataggagg tacaccatcc tggactatgg cagtggacct     1200
ggatatcata tcacggaaga tggcaaacgt tacgaaccta cagaggaaga tttgaaagac     1260
atcaatttcc gctacgcatc ggcagcgccc aagcattcag ttacccatga tggcacagac     1320
gttggtattt gggtcaacgg acctttcgct catctcttca cgggtgtcta tgaagagaat     1380
tacattcccc acgccttggc ctacgcagcc tgcgttggta caggacgcac tttctgtgac     1440
gaaaaatgag atgtagatga ttaccttctt aagtacatta aagattgcaa aaaaaaaaa     1500 aaaaaaaaaa a                                                          1511
```

```
<210> SEQ ID NO 23
<211> LENGTH: 26
<212> TYPE: DNA
<213> ORGANISM: Artificial Sequence
<220> FEATURE:
<223> OTHER INFORMATION: Primer

<400> SEQUENCE: 23
gcgtggtgca tatggtcaat ccgtcc                                            26

<210> SEQ ID NO 24
<211> LENGTH: 32
<212> TYPE: DNA
<213> ORGANISM: Artificial Sequence
<220> FEATURE:
<223> OTHER INFORMATION: Primer

<400> SEQUENCE: 24
atggagctca acccaatcac cgaagaagac aa                                     32

<210> SEQ ID NO 25
<211> LENGTH: 30
<212> TYPE: DNA
<213> ORGANISM: Artificial Sequence
```

-continued

```
<220> FEATURE:
<223> OTHER INFORMATION: Primer

<400> SEQUENCE: 25
atgaagcttt cattttcgt cacagaaagt                                              30
```